(12) United States Patent
Gokaraju et al.

(10) Patent No.: US 10,471,114 B2
(45) Date of Patent: Nov. 12, 2019

(54) COMPOSITION FROM SPHAERANTHUS INDICUS AND GARCINIA MANGOSTANA FOR THE CONTROL OF METABOLIC SYNDROME

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Kiran Bhupathiraju, Vijayawada (IN); Krishanu Sengupta, Vijayawada (IN); Venkata Krishna Raju Alluri, Vijayawada (IN)

(73) Assignee: LAILA NUTRACEUTICALS, Labbipet Vijayawada (IN)

( * ) Notice: Subject to any disclaimer, the term of this patent is extended or adjusted under 35 U.S.C. 154(b) by 784 days.

(21) Appl. No.: 14/951,175

(22) Filed: Nov. 24, 2015

(65) Prior Publication Data

US 2016/0074457 A1 Mar. 17, 2016

Related U.S. Application Data

(62) Division of application No. 13/146,965, filed as application No. PCT/IN2010/000053 on Feb. 1, 2010, now Pat. No. 9,241,964.

(30) Foreign Application Priority Data

Feb. 9, 2009 (IN) .............................. 224/CHE/2009

(51) Int. Cl.
*A61K 36/38* (2006.01)
*A61K 36/28* (2006.01)
*A61K 35/12* (2015.01)
*A23L 33/105* (2016.01)

(52) U.S. Cl.
CPC ............ *A61K 36/38* (2013.01); *A23L 33/105* (2016.08); *A61K 35/12* (2013.01); *A61K 36/28* (2013.01); *A23V 2002/00* (2013.01)

(58) Field of Classification Search
None
See application file for complete search history.

(56) References Cited

U.S. PATENT DOCUMENTS

| 2006/0057229 A1 | 3/2006 | Inomata et al. |
| 2008/0254157 A1 | 10/2008 | Chauhan et al. |

FOREIGN PATENT DOCUMENTS

| JP | 07138126 A | 5/1995 |
| JP | 09110688 A | 4/1997 |
| JP | 2005298379 A | 10/2005 |
| WO | 2006134609 A2 | 12/2006 |

OTHER PUBLICATIONS

"Our care: Pre-Diabetes (Hyperglycemia)". Internet archive date: Jul. 14, 2011. Retrieved from the Internet on: Aug. 27, 2018. Retrieved from: <URL: http://patients.dartmouth-hitchcock.org/endo/pre-diabetes.html>. (Year: 2011).*
International Search Report dated Aug. 25, 2010 for WO2010/100653 (PCT/IN2010/000053).
Bafna, et al., "ARS Pharmaceutica", 45:3, 2004, 281-291.
Jadhav, et al., "Indian Journal Chem", vol. 46B, 2007, 379-381.

* cited by examiner

*Primary Examiner* — Amy L Clark
(74) *Attorney, Agent, or Firm* — Kramer Amado, P.C.

(57) ABSTRACT

Pharmaceutical/dietary supplements and food ingredient(s) derived from *Sphaeranthus indicus* are used for controlling or treating a metabolic disorder. The supplements and food ingredient(s) are selected from *Sphaeranthus indicus* extract(s), fraction(s), active compound(s) and phytochemical(s) or mixtures thereof and their compositions, preferably in combination with at least one component selected from the extract(s), fraction(s), active compound(s) and phytochemical(s) or mixtures thereof derived from *Garcinia mangostana*. The ingredients and the composition(s) can be used for the control, prevention and treatment of obesity, metabolic syndrome, diabetes and other metabolic disorders, and also to regulate energy expenditure, prevention of atherosclerotic plaques in coronary artery and abdominal aorta, increase insulin sensitivity, improve glucose tolerance, lower triglyceride levels and balance glucose levels in mammals.

10 Claims, 10 Drawing Sheets

COMPOSITION FROM SPHAERANTHUS INDICUS AND GARCINIA MANGOSTANA FOR THE CONTROL OF METABOLIC SYNDROME

RELATED APPLICATIONS

This application is a divisional of U.S. application Ser. No. 13/146,965 filed Jul. 29, 2011, which is a U.S. National Stage of International Application No. PCT/IN2010/000053 filed Feb. 1, 2010, now published as WO/2010/100653. The entire disclosure of each prior application is incorporated by reference herein in their entirety.

FIELD OF INVENTION

The present invention relates to novel pharmaceutical or dietary supplement compositions comprising at least one component selected from the extract(s), fraction(s), active compound(s), phytochemical(s) or mixtures thereof derived from *Sphaeranthus indicus* and at least one component selected from the extract(s), fraction(s), active compound(s), phytochemical(s) or mixtures thereof derived from *Garcinia mangostana*, optionally containing one or more of pharmaceutically and dietically acceptable diluents, vehicles, carriers ad actives or mixtures thereof.

The invention further relates to the use of at least one component selected from the extract(s), fraction(s) and active compound(s), phytochemical(s) or mixtures thereof derived from *Sphaeranthus indicus* or their compositions, preferably in combination with at least one component selected from the extract(s), fraction(s) and active compound(s), phytochemical(s) or mixtures thereof derived from *Garcinia mangostana* for the control, prevention and treatment of metabolic syndrome or obesity, and/or one or more disease indications related to or associated with metabolic syndrome and metabolic disorders.

The invention also relates to the amelioration of one or more of the biomarker proteins or metabolic processes related to metabolic syndrome, obesity and other related or associated disease conditions by the *Sphaeranthus indicus* derived component(s) or their compositions.

BACKGROUND OF THE INVENTION

*Sphaeranthus indicus* belongs to the family Asteraceae. It is also known as Gorakhmundi. It is a highly branched, strongly-scented annual herb with winged stem and toothed wings. Leaves are obovate-oblong, narrowed at the base, dentate and serrate. Flowers are compound heads, globose ovoid. The flowering time spans from November to January in Indian conditions. The medicinally useful parts are root, bark, leaves, flowers, and seeds.

The flowering and fruiting heads of the plant, *Sphaeranthus indicus* contains 3a-hydroxy-5a,9-dimethyl-3-methylene-3a,4,5,5a,6,7,8,9b-octahydro-3H-naphtho[1,2-b]furan-2-one (7-α-Hydroxy-4,11(13)-eudesmadien-12,6-olide or 7-hydroxyfrullanolide) as a major compound. It strongly inhibits pro-inflammatory cytokines.

Several other compounds have been reported from *Sphaeranthus indicus* like methyl chavicol, α-ionone, δ-cadinene, p-methoxycinnamaldehyde as major constituents and α-terpinene, citral geraniol, geranyl acetate, β-ionone, sphaerene, indicusene and sphaeranthol as minor constituents of essential oil (Perfum. Essent. Oil Record. 1959, 50, 765; Chem. Abstr. 1960, 54, 798Og); 7α-hydroxy-eudesm-4en-6,12-olide, its β-isomer, dihydrolactone, a new sesquiterpene acid, 2-hydroxycostic acid, β-eudesmol and illicic acid (Jayant S. Sohoni et *J. Chem, Soc., Perkin Trans*, 1, 1988, 157-160); Eudesmanoids like 11-alpha-13-dihydro-3alpha,7alpha-dihydroxy-4,5-epoxy-6 beta,7-eudesmanolide, 11 alpha,13-dihydro-7alpha-acetoxy-3beta-hydroxy-6beta,7-eudesm-4-enolide and 3-keto-beta-eudesmol (Pujar P P et al, *Fitoterapia*. 2000 June; 71(3):264-8) and a sesquiterpene glycoside (Shekhani M S et al, 1990; Phytochemistry 29, 2573-2576).

Some of the non-patent literature of *Sphaeranthus indicus* is quoted below:

In a study evaluating the anti-inflammatory effects of *Rubia cordifolia, Curcuma longa, Hemidesmus indicus, Azadirachta indica* and *Sphaeranthus indicus, Sphaeranthus* was found to be more potent in suppressing the proinflammatory cytokines interleukin-8 (IL-8) and tumor necrosis factor α (TNF α) induced by the culture supernatant of *Propionibacterium acnes* in polymorphonuclear leukocytes (PMNL) and monocytes [Jain A et. al.; *Phytomedicine*. 2003 January; 10(1):34-8].

The petroleum ether extract from the flower heads of *Sphaeranthus indicus* Linn was found to be effective in increasing phagocytic activity, hemagglutination antibody titer and delayed type hypersensitivity when tested in mice. The petroleum extract showed a dose-response relationship. It was found that 200 mg/kg dose was the optimum dose. *Sphaeranthus* acts as an immunomodulatory agent, by stimulating both humoral and cellular immunity as well as phagocytic function. [Bafna A R et. al; *J Herb Pharmacother*. 2007; 7(1):25-37].

In a study, the effect of aqueous extract of *Sphaeranthus indicus* (300 mg/kg/day, i.p) against dexamethasone (10 mg/kg/day, s.c) induced changes in lipid profile in rat was investigated. *S. indicus* showed significant decrease in serum total cholesterol, triglyceride, LDL, VLDL and there was no significant change in the level of HDL. Atherogenic index also reduced significantly after *S. indicus* treatment thus indicating that, *S. indicus* has a potential lipid lowering effect [Tenpe C R et al; Biomed. Vol. 02 (4), 2008; 400-403].

Recently, in another study, the antihyperglycaemic effects of *Sphaeranthus indicus* in rats rendered diabetic by nicotinamide [120 mg kg(−1) i.p.] and streptozotocin (STZ) [60 mgkg(−1) i.p] was investigated. Oral administration of *S. indicus* for 15 days resulted in significant decrease in blood glucose levels and increases in hepatic glycogen and plasma insulin levels. Fasting normal rats treated with the alcoholic extract of *S. indicus* showed significant improvement in oral glucose tolerance test. Glibenclamide was used as a reference standard [Prabhu K S et al; *J Pharm Pharmacol*. 2008; 60(7): 909-16].

None of the above literature describes the amelioration of metabolic syndrome related biomarkers or its therapeutic effects against metabolic syndrome or disease conditions associated with metabolic syndrome by *Sphaeranthus indicus*.

Aqueous extract of *Sphaeranthus indicus* has been used in Tenpe C R et al study, which do not contain significant quantities of 7-hydroxyfrullanolide, whereas the present inventive compositions contain lipophilic extract comprising 7-hydroxyfrullanolide as active compound. Hence the inventive compositions are different from those used in the Tenpe C R et al study. Similarly, alcoholic extract of roots and stolons has been used in Prabhu K S et al's study. However, the present inventive compositions are derived from flower heads, which contain predominantly 7-hydroxyfrullanolide and hence are different from those used in the Prabhu K S et al's study.

Some of the Patent literature of *Sphaeranthus* is quoted below:

PCT Publication WO07036900A2 relates to a novel herbal composition comprising an extract of flowering and fruiting heads of the plant, *Sphaeranthus indicus* containing 3a-hydroxy-5a,9-dimethyl-3-methylene-3a,4,5,5a,6,7,8,9b-octahydro-3H-naphtho[1,2-b]furan-2-one (7-Hydroxy-4,11 (13)-eudesmadien-12,6-olide), as a bioactive marker. The said invention also relates to methods of manufacture of the said compositions.

Japanese Patent Publication JP07138180A2 relates to inhibitor of hyaluronidases containing an extract separated from at least one herb selected from the group consisting of *Azadirachta indica, Cymbopogon nardus, Murraya koenigii, Sphaeranthus indicus, Ocimum sanctum, Tinospora cordifolia* and *Phyllanthus nuriri* and its use as a cosmetic capable of preventing aging and preventing fine wrinkles and dryness of the skin.

PCT Publication WO06134609A2 discloses herbal anticancer agent comprising the extract of plant *Sphaeranthus indicus* or group of compounds obtained from the plant *Sphaeranthus indicus*. It also discloses a pharmaceutical composition comprising the said agent, methods for preparing the composition, methods of treating all kinds of cancer in mammals including human beings, methods of making the plant extract and methods for obtaining the active constituents.

PCT Publication WO06016228A2 relates to a compound or group of compounds present in an active principle derived from plants of the species *Sphaeranthus*, for the preparation of pharmaceutical formulations or food supplements for the prophylaxis and/or treatment of tumor diseases. The said invention furthermore relates to a novel method for the isolation of an active principle from *Sphaeranthus* plant parts which are effective in prophylaxis and/or treatment of cancers.

U.S. Pat. No. 7,344,738 provides pharmaceutical or medicinal preparation comprising a combination of two herbal compositions, including one comprising a mixture of the following herbs: *Moringa oleifera, Boerhavia diffusa, Onosma bracteatum, Bauhinia variegata, Spheranthus indicus, Tecomella undulata, Chlorophytum borivilianum, Ficus racemosa,* and *Cyperus rotundus,* or a mixture of the active ingredients that have been extracted from those herbs or chemically synthesized. The herbal preparation is effective for the treatment of a wide range of physiological and pathological conditions in the human body resulting from a weakened or deteriorating immune system.

*Garcinia mangostana* which is also used in the present novel composition belongs to the family Guttiferae. *Garcinia* consists of roughly 300 species of dioecious trees and shrubs distributed into South America (where they are also known as Rheedia), Africa, Madagascar, and Southeast Asia. Most of the species diversity in the genus is centered in Malaysia, with over two-thirds of the species in the genus being found there [http://www.mobot.org/MOBOT/Research/mangosteen/].

Mangostins are a major class of compounds in *Garcinia mangostana*. The structure of mangostin was established by Peter Yates et al. [Peter Yates, George H. Stout; *J. Am. Chem. Soc.*; 1958; 80(7); 1691-1700].

Several pharmacological activities have been reported for mangosteen like anti-inflammatory [Gopalakrishnan C et al., *Indian J Exp Biol.* 1980 August; 18(8):843-6], histaminergic and a serotonergic receptor blocking agent [Chairungsrilerd N et al., *Planta Med.* 1996 October; 62(5):471-2], anti-cancer agent [Ee G C et al., *J Asian Nat Prod Res.* 2008 May; 10(5):481-5], Anti-microbial [Sundaram B. M., et al.; *Planta Med.* 1983; 48:59-60], etc. and a lot of research is being conducted for exploring new activities.

Some of the non-patent literature of *Garcinia* is described below:

In an assay guided fractionation study, the different fractionations from lipophilic to hydrophilic using combined solvent extraction and Amberlite XAD2 adsorption chromatography was studied. The mangosteen pericarps extracts have been tested for alpha-amylase inhibition activity and it was concluded that xanthones does not have any inhibiting activity but the Oligomeric Proantho Cyanidins from the hydrophilic fraction are reported to be 56 times more effective in inhibiting alpha-amylase. [Eng Kiat Loo A, Huang D.; *J Agric Food Chem.* 2007 sNov 28; 55(24):9805-10].

It is of importance to know that in the above stated study [Eng Kiat Loo et al, 2007], the alpha-amylase inhibitory activity was attributed to oligomeric proantho cyanidins. It was further stated that xanthone fraction did not have any alpha-amylase inhibition activity. Hence the active compound(s) responsible for the activity of the extracts or fractions of this prior art article are different from those of the present invention.

In another study the investigators determined Aldose Reductase (ALR2) inhibitory effect of *G. mangostana*. α-Mangostin was found to be potent against ALR2. It was concluded that α-mangostin might be useful in preventing diabetic complications [Sri Fatmawatia et al., Biology, Chemistry, Pharmacology and Clinical Studies of Asian Plants Apr. 9-11, 2007, Surabaya, Indonesia].

A cursory review of prior art reveals that, there is no knowledge relating to the use of the composition comprising *Sphaeranthus indicus* and *Garcinia mangostana* for treating Metabolic Syndrome or for ameliorating metabolic marker proteins.

Metabolic Syndrome also known as Syndrome X, insulin resistance syndrome and DysMetabolic Syndrome is a condition, wherein a group of diseased states, which increase atherosclerosis, stroke and diabetes.

Metabolic Syndrome was first described by Reaven in 1988 [Reaven, (1988) Diabetes 37; 1595-1607] as a cluster of interrelated common clinical disorders, including obesity, insulin resistance, glucose intolerance, hypertension and dyslipidemia.

A criteria for diagnosing Metabolic Syndrome was established by The Adult Treatment Panel-III (ATP-III) of the National Cholesterol Education Program in 2001 [JAMA (2001), 285; 2486-2497]. Five Criteria were selected by this Panel to identify individuals with Metabolic Syndrome including abdominal obesity, impaired fasting glucose, high triglyceride (TG), low HDL cholesterol (HDL-C) concentrations and increased blood pressure. Metabolic Syndrome is diagnosed, if any three of the components are present in an individual.

A lot of research is being carried out over a decade to develop agents to control Metabolic Syndrome. The application of metabolic markers for the control of this syndrome has also been attempted.

People with Metabolic Syndrome are at high risk of coronary heart disease, other diseases related to plaque buildups in artery walls (e.g., stroke and peripheral vascular disease) and type-2 diabetes.

Some of the biological conditions are also considered as markers for Metabolic Syndrome, which include Hyperuricemia—[Vuorinen-Markkola H et al; *J Clin Endocrinol Metab.* 1994; 78(1):25-9.]; Hypertriglyceridemia [Grundy S M.; *Am J Cardiol.* 1998; 81(4A):18B-25B]; Hypoadiponectinemia [Stern N et al; *J Cardiometab Syndr.* 2007; 2(4): 288-94]; Microalbuminuria [Brahimi M et al; *Arch Mal Coeur Vaiss.* 2007; 100(8):673-6.].

Some of the patents are quoted below which refer to the treatment and curing of Metabolic Syndrome.

PCT Publication WO08086403A1 describes the identification and isolation of chromones and novel chromone compositions from plant sources that are effective in enhancing adiponectin production by adipocytes and regulating genes involved in fatty acid biosynthesis. The invention also include methods for the prevention and treatment of a variety of diseases and conditions including, but not limited to insulin resistance, glucose intolerance, hyperglycemia, Metabolic Syndromes, dyslipidemia, and hypertriglyceridemia.

PCT Publication WO08074935A2 relates to compositions and products that can be obtained from plants, such as extracts, fractions and/or molecules useful for preventing or treating metabolic disorders, obesity and/or diseases associated therewith such as the X syndrome (Metabolic Syndrome), type-2 diabetes, or for producing food additives for human beings or animals.

PCT Publication WO08093848A1 discloses a pharmaceutical product containing phosphatidylcholine derived from soybean for oral administration or for oral cavity application, a functional food and an oral composition which can prevent or ameliorate a disorder in the physical function induced by the increase in an inflammation marker, which can reduce the occurrence of Metabolic Syndrome or the risk of a disease and Metabolic Syndrome, and which can maintain or promote the healthy state.

Based on the information cited above and several other documents, the inventors of the present invention have felt the need of an effective natural composition which can efficiently be used for the control of Metabolic Syndrome and several other associated and related diseases.

According to our knowledge, there is no prior art relating to the usage of ingredients selected from the extracts, fractions or active compounds, phytochemical(s) or mixtures thereof derived from *Sphaeranthus indicus* and their compositions in combination with ingredients selected from the extracts, fractions or active compounds, phytochemical(s) or mixtures thereof derived from *Garcinia mangostana* for the amelioration of for the control, prevention and treatment of disease conditions associated with or related to obesity, metabolic Syndrome and other metabolic disorders.

SUMMARY OF THE INVENTION

In the primary aspect, the invention provides novel pharmaceutical/dietary supplement/food ingredient compositions comprising at least one component selected from the extract(s), fraction(s), active compound(s) and phytochemical(s) or mixtures thereof derived from *Sphaeranthus indicus* and at least one component selected from the extract(s), fraction(s), active compound(s) and phytochemical(s) or mixtures thereof derived from *Garcinia mangostana*, optionally containing one or more of pharmaceutically and dietetically acceptable phytochemical actives, diluents, vehicles, carriers and actives or mixtures thereof.

In the other primary aspect, the invention provides the use of at least one pharmaceutical/dietary supplement/food ingredient component selected from the extract(s), fraction(s), active compound(s) and phytochemical(s) or mixtures thereof derived from *Sphaeranthus indicus* or their compositions, preferably in combination with at least one component selected from the extract(s), fraction(s) and active compound(s) and phytochemical(s) or mixtures thereof derived from *Garcinia mangostana* for the control, prevention and treatment of metabolic syndrome or obesity, and/or one or more disease indications related to or associated with metabolic syndrome.

In the other aspect, the invention provides *Sphaeranthus indicus* derived component(s) selected from the extract(s), fraction(s), active compound(s) and phytochemica(s) or mixtures thereof or their compositions, preferably in combination with at least one component selected from the extract(s), fraction(s), active compound(s) and phytochemical(s) or mixtures thereof derived from *Garcinia mangostana* for the amelioration of the expression or production of one or more biological marker proteins related to or associated with metabolic syndrome, obesity and other disease conditions associated with metabolic syndrome including but not limited to Matrix Metalloproteinase-1 (MMP-1), Matrix Metalloproteinase-3 (MMP-3), Peroxisome proliferator-activated receptor gamma (PPARγ), Adipose Differentiation Related Protein (ADRP), adipocyte CD36, Macrophage CD36, Monocyte Chemotactic protein (MCP-1), Oxidized LDL (Ox-LDL), adipocyte fatty-acid-binding protein (aP2/FABP4/A-FABP), beta-3 Adrenergic Receptor (β3AR), Perilipin, Adiponectin and Protein tyrosine phosphatase-1B (PTP-1B).

In a further aspect, the invention provides *Sphaeranthus indicus* derived component(s) selected from the extract(s), fraction(s), active compound(s) and phytochemical(s) or mixtures thereof or their compositions, preferably in combination with at least one component selected from the extract(s), fraction(s) and active compound(s) derived from *Garcinia mangostana* for the amelioration of the metabolic processes such as promotion of lipolysis, and inhibition of adipogenesis, alpha-amylase enzyme and alpha-glucosidase enzyme activities.

In a major important aspect of the invention, pharmaceutical/dietary supplement/food ingredient(s) the extracts, fraction(s), pure compounds or phytochemicals or mixtures thereof derived from *Sphaeranthus indicus* or the compositions comprising the said ingredients for the control, prevention and treatment of metabolic syndrome or obesity, and/or one or more disease indications related to or associated with metabolic syndrome.

In other major aspect of the invention the extracts or enriched fractions or pure compounds or the mixtures thereof derived from *Sphaeranthus indicus* can be used alone or in combination with one or more of pharmaceutically or dietically acceptable vehicle or carrier or diluents or mixtures thereof for the prevention, control and treatment of metabolic syndrome or obesity and/or one or more disease conditions related to or associated thereof.

In a further aspect of the invention the active compound responsible for activity of *Sphaeranthus indicus* for prevention, control and treatment of metabolic syndrome and obesity and other related and associated conditions including but not limited to, 7-hydroxyfrullanolide; 11α,13-dihydro-3α,7α-dihydroxy-4,5-epoxy-6β,7-eudesmanolide; 11α,13-dihydro-7α-acetoxy-3β-hydroxy-6β,7-eudesm-4-enolide; 3-keto-β-eudesmol; 11α,13-dihydro-3α,7α-dihydroxyuedes-4-en-6α,12-olide; 11α,13-dihydro-3α,7α-dihydroxyfrullanolide; 11α,13-dihydro-7α,13-dihydroxyfrullanolide; 11α,13-dihydro-7α,-hydroxy-13-methaoxyfrullanolide; 2α,7α-dihydroxy-4-en-11,13-dihydroeudesn-6,12-olide; 2α-hydroxycostic acid; 3keto, 7α-hydroxyeudesm-4-en-6,12-olide (cryptomeridiol); 4-epicryptomeridiol; Sphaeranthanolide; 2α-hydroxysphaerantholide; 2α-Acetoxysphaerantholide; 2α,7α-Dihydroxysphaerantholide; 2α-Acetoxy-7α-hydroxysphaerantholide; 2α-Acetoxy-5α-hydroxyisosphaerantholide etc., preferably 7-hydroxyfrullanolide or related compounds or its analogs or mixtures thereof.

In the other aspect, the source of 7-α-hydroxy-4, 11(13)-eudesmadien-12,6-olide (7-hydroxyfrullanolide) used in the present invention can be *Sphaeranthus indicus* or any plant source or synthesis.

In other aspect of the invention, the *Sphaeranthus indicus* derived components and their compositions can be used effectively for the prevention, treatment and control of one or more conditions selected from but not limited to Metabolic Syndrome, obesity, atherosclerosis, diabetes, insulin resistance, regulate energy expenditure, prevention of atherosclerotic plaques in coronary artery and abdominal aorta, increase insulin sensitivity, improve glucose tolerance, lower triglyceride levels and balance glucose levels in mammals.

In another aspect, the present invention provides compositions comprising at least one component selected from the extract(s), fraction(s), active compound(s) and phytochemical(s) or mixtures thereof derived from *Sphaeranthus indicus* in combination with at least one component selected from the extract(s), fraction(s), active compound(s) and phytochemical(s) or mixtures thereof derived from *Garcinia mangostana* to produce synergistic effects to prevent or control or treat metabolic syndrome or disease conditions associated with metabolic syndrome, and for amelioration of the production of different biological marker proteins associated with metabolic syndrome or disease conditions associated with metabolic syndrome.

In the other aspect, the invention provides methods for the prevention, treatment and control of Metabolic Syndrome, obesity and other disease conditions associated with or related to metabolic syndrome, especially, diseases and conditions mediated by insulin resistance in mammals, wherein the method comprises of administering to a subject in need thereof an effective amount of a pharmaceutical or dietary supplement selected from the extracts, fractions, active compounds and phytochemicals(s) or mixtures thereof derived from *Sphaeranthus indicus* optionally containing at least one component selected from pharmaceutically or dietetically acceptable vehicles, carrier, diluent and actives and mixtures thereof.

In the other aspect, the invention provides methods for the prevention, treatment and control of Metabolic Syndrome, obesity and other disease conditions associated with or related to metabolic syndrome, especially, diseases and conditions mediated by insulin resistance in mammals, wherein the method comprises of administering to a subject in need thereof an effective amount of a pharmaceutical or dietary supplement selected from the extracts, fractions, active compounds and phytochemical(s) or mixtures thereof derived from *Sphaeranthus indicus*, preferably in combination with at least one component selected from the extract(s), enriched fraction(s) or pure compound(s) derived from *Garcinia mangostana*, optionally containing at least one component selected from pharmaceutically or dietetically acceptable vehicles, carrier, diluent and actives and mixtures thereof.

DETAILED DESCRIPTION OF THE INVENTION

Figure 1:
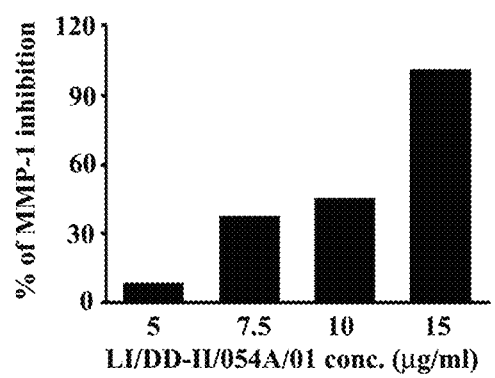
FIG. 1: Illustrates Bar diagram which shows percent reduction in MMP-1 in A2058 human melanoma cell culture supernatants obtained by *Sphaeranthus indicus* ethyl acetate extract (LI/DD-II/054A/01). A2058 cells were induced with 50 nM PMA in absence or presence of different concentrations of LI/DD-II/054A/01 for 24 h as indicated. Secreted MMP-1 concentration in the cell free culture supernatants was measured using MMP-1 ELISA Development Kit (R&D System, Minneapolis, Minn., USA). The MMP-1 concentration in culture supernatants was estimated quantitatively from the standard curve generated using known concentrations of MMP-1. Percentage of MMP-1 inhibition at each concentration of test compound was calculated from the formula: {(Conc. of MMP-1 in PMA induced−Conc. of MMP-1 in the test well)×100}÷Conc. of MMP-1 in PMA induced wells.

Obesity is excess body weight for a particular age, sex and height as a consequence of imbalance between energy intake and energy expenditure. The primary causes of obesity are either due to overeating, inadequate exercise or eating disorder, some genetic disorders, underlying illness (e.g. hypothyroidism), certain medications or sedentary lifestyle. Obesity increases the risk of many diseases and health conditions such as hypertension, dyslipidemia (for example, high total cholesterol or high levels of triglycerides), type 2 diabetes, coronary heart disease, stroke, gallbladder disease, osteoarthritis, sleep disorders, respiratory problems, tumors (endometrial, breast, and colon), arteriosclerosis and heart failure.

Metabolic syndrome is a condition involving a set of disorders that enhances the risk of heart disease. The major components of metabolic syndrome are excess weight, the cardiovascular parameters (high blood pressure, dyslipidemia, high levels of triglycerides and low levels of HDL in the blood), atherosclerosis, diabetes and insulin resistance. A subject suffering with several of these components, i. e. metabolic syndrome is highly prone to heart disease, though each component is a risk factor.

Adipocytes and macrophages play important role in the pathogenesis of metabolic syndrome and disease components associated with it. They both share a number of common features, including the ability to phagocytize and kill microorganisms and to secrete cytokines such as tumor necrosis factor (TNF) and interleukin-1(IL-1). Critical transcription factors in adipocytes involved in regulating the expression of cytokines, inflammatory molecules, and fatty acid transporters are also expressed and have similar biologic roles in macrophages. For example, activation of PPAR, a member of the nuclear-receptor super-family of ligand-activated transcription factors, is associated with differentiation of both types of cells. In adipocytes, PPAR regulates adipocyte development and glucose homeostasis. In macrophages, PPAR regulates expression of inflammatory genes and is involved in the development of atherosclerotic lesions.

The macrophages over express Matrix Metalloproteinase-1 (MMP-1) and Matrix Metalloproteinase-3 (MMP-3) under certain disease conditions associated with metabolic syndrome. Similarly, the adipocytes in addition to accumulating fat during the obesity development produce and circulate several low molecular weight bioactive protein molecules having powerful effects throughout the body. These protein markers are related to different components of metabolic syndrome. The expression and production of several of these metabolic markers, which include but not limited to PPAR-γ, Adipose Differentiation Related Protein (ADRP), CD36, Adipocyte Fatty-Acid-Binding Protein (aP2/FABP4/A-FABP), Beta-3 adrenergic receptor (β3-AR), adiponectin and Perilipin, become abnormal during obesity and metabolic syndrome and other disease conditions associated with metabolic syndrome.

Atherosclerosis, also known as coronary heart disease (CHD), is one of the major vascular complication and important component of metabolic syndrome that has enormous impact on the human health. It is a chronic inflammatory reaction to modified lipoproteins, primarily oxidized low density lipoproteins (Ox LDL). Atherosclerosis is thought to develop as a result of lipid uptake by vascular-wall macrophages leading to the development of foam cells and the elaboration of cytokines and chemokines resulting in smooth muscle-cell proliferation (Berliner, J. A., Circulation, 91: 2488-2496, 1995, Boring, L., et. al., Nature, 394: 894-897, 1998). Cluster of Differentiation 36 (CD36) protein has been proven to play a key role in the process of atherosclerosis.

A brief description of some of the metabolic biomarker molecules, digestive enzymes and the metabolic processes that are involved in the pathogenesis and control of metabolic syndrome and the disease conditions associated is outlined below:

1. Matrix Metalloproteinases:

Matrix Metalloproteinases (MMPs) are zinc dependent endopeptidases, that are capable of breaking down all kinds of extra cellular matrix proteins, such as collagen, that are normally found in the spaces between cells in tissues. MMPs are divided primarily into three principal groups, the fibroblast collagenase-1 (MMP-1) formed of the collagenases, the gelatinases comprising gelatinase A (MMP-2) and the gelatinase B (MMP-9), and the stromelysines comprising stromelysine-1 (MMP-3) and matrilysine (MMP-7). An excess of metalloproteinase leads to degradation of biomolecules such as collagen, proteoglycon and gelatin, which can have fatal consequences on epidermis and can also generate diseases of the cartilages, inflammation etc.

MMPs are thought to participate in the pathogenesis of coronary artery disease (CAD), particularly in the occurrence of acute coronary syndrome (ACS). Studies show that the expression and regulation of MMPs and their tissue inhibitors (TIMPs) were evaluated in premature CAD. The plasma concentrations/activities of MMP-2, MMP-3 and MMP-9, TIMP-1, and TIMP-2 in 80 patients (49 with ACSs and 31 with stable CAD) and 40 controls were evaluated in clinical study and it was concluded that MMP and TIMP plasma levels in premature CAD are linked to clinical presentation and markers of inflammation and metabolic disorders rather than to genetic polymorphisms. Similarly, macrophage-activity (monocyte chemoattractant prtein-1, neopterin), tissue-remodeling (matrix metalloproteinase-9) and thrombosis (tissue-factor) related biomarkers were found to be consistently elevated in Acute Coronary Syndrome (ACS) compared to stable coronary artery disease (CAD)

The role of MMPs [both positive and negative] in obesity and in the development of adipose tissue has been investigated by several investigators. A few are quoted below: In a study the investigators studied the differential expression of MMPs and TIMPs by Northern blot and real-time PCR in two genetic models of obesity (ob/ob and db/db mice) and in a diet-induced model of obesity (AKR mice). They have concluded that mRNA levels for MMP-2, MMP-3, MMP-12, MMP-14, MMP-19, and TIMP-1 are strongly induced in obese adipose tissues compared with lean tissues [Chavey C et al., J Biol Chem. 2003; 278(14):11888-96].

In a similar study on nutritionally induced obesity mouse, the expression of MMP-3, -11, -12, -13, and -14 and TIMP-1 mRNAs was found to be upregulated when compared to those on the standard diet. It was also observed in an in vitro study that the adipogenesis was reduced in the presence of a synthetic MMP inhibitor [Maquoi E et al., Diabetes. 2002; 51(4):1093-101].

2. Peroxisome Proliferator-Activated Receptor (PPAR)-γ:

Peroxisome proliferator-activated receptor γ (PPAR γ) is a nuclear receptor that plays a pivotal role in obesity and diabetes. An increase in adipose tissue mass can be the result of the production of new fat cells through the process of adipogenesis and the deposition of increased amounts of cytoplasmic triglyceride or lipid droplets per cell. In the adipogenesis process, proliferation of preadipocytes or precursor fat cells is followed by the differentiation of these cells to the mature adipocyte phenotype. PPAR γ is expressed predominantly in adipose tissue, wherein it is known to play a critical role in adipocyte differentiation and fat deposition.

The activation of PPAR γ on the other hand leads to an improvement of insulin action. PPAR γ is the molecular target of the thiazolidinedione (TZD) class of antidiabetic drugs, such as troglitazone (Rezulin), rosiglitazone (Avandia), and pioglitazone (Actos). Adipose tissue development and insulin sensitivity were found to be greatly impaired in PPAR γ2 knockout mice indicating its role in obesity and diabetes. PPAR γ is a key regulator of fatty acid uptake and lipogenesis in addition to adipose cell differentiation through its influence on the production of the enzymes required for lipid storage and metabolism (Zhang, J., Proceedings of National Academy Sciences 2004; 101; 10703-10708, 2004).

3. Adipose Differentiation Related Protein (ADRP):

ADRP is a 50 kD protein and it's mRNA (ADRP mRNA), which is 1.7 Kb in size, is expressed at high level in adipose tissue. The expression of ADRP is very low in undifferentiated adipocytes, but ADRP mRNA reaches 50 to 100-fold in few hours after the onset of adipose differentiation process. ADRP is also found in many different types of cells and tissues that accumulate or synthesize lipids. The above thus indicate the possible role of ADRP in the formation or stabilization of lipid droplets in adipocytes and other cells. ADRP specifically enhances uptake of long chain fatty acids by adipose tissue. Hence ADRP is an important target to identify the compounds that can potentially control obesity and diabetes through regulation of the expression of ADRP.

4. Adipocyte CD36:

CD36 is a common protein marker expressed by both adipocytes and macrophages. The CD36 expressed in adipocytes is known to function as a fatty acid transporter (FAT). Studies on adipocytes showed that CD36 mRNA is a marker of adipocyte differentiation. It is a scavenger receptor that binds and internalizes oxidized LDL (Ox LDL) in macrophages. CD36 also functions as a long-chain fatty acid (LCFA) transporter to facilitate the uptake of LCFAs in adipocytes. The CD36 expression is up-regulated by PPAR during the differentiation of both types of cells. It is also shown that the adipocytes can endocytose and lysosomally degrade Ox LDL, mainly mediated by CD36. The CD36 null animals showed significant decrease in binding and uptake of oxidized low density lipoprotein and showed significant increase in fasting levels of cholesterol, nonesterified free fatty acids, and triacylglycerol.

5. Macrophage CD36:

CD36 is a prototypic member of the class B scavenger receptor family. The endogenous (e.g., macrophages, adipocytes, platelets, microvascular endothelial cells and specialized epithelial cells) and ectopic (e.g., melanoma cells and fibroblasts) expression of this multi-ligand receptor on the surface of cells confers phagocytic activity for engulfment of apoptotic cells. CD36 is widely expressed and may interact with multiple extracellular ligands including thrombospondin-1 (TSP-1), long chain free fatty acids (FFAs), modified (oxidized) low-density lipoprotein (Ox-LDL), advanced glycation end (AGE) products, collagen I and collagen IV [PLoS Medicine, 2: 152-161, 2005]. CD36 is expressed on the surface of monocytes and macrophages and mediates uptake of oxidized low-density lipoprotein (Ox-LDL) [Nozaki, S., J. Clin. Invest. 96: 1859-1865, 1995] as well as to play a role in diverse cellular processes including foam cell formation, fatty acid transport, engulfment and removal of senescent cells, suppression of angiogenesis, and cell-matrix interactions. The CD36-dependent uptake of Ox-LDL has been shown to be critical to cholesterol accumulation and subsequent foam cell formation; activities that likely contribute to the observed involvement of CD36 in mouse models of atherogenesis [Michael E et al, J. Exp. Med., 203: 2613-25, 2006].

CD36 may initiate atherosclerotic lesions and be an important risk factor of cardiovascular disease. In mice lacking the CD36 receptor, foam-cell formation and vascular lesion development were indeed interrupted [Febbraio M., et. al., J Clin Invest 105:1049-1056, 2000]. Hyperglycemia-induced synthesis of CD36 in macrophages has been associated with increased uptake of Ox-LDL by macrophages and foam cell formation in atherosclerotic lesions in people with diabetes (PLoS Medicine, 2: 152-161, 2005). The increased Peroxisome proliferator-activated receptor-γ (PPAR-γ) obtained in response to high glucose levels lead to an increased expression of CD36 in macrophage and contribute accelerated atherosclerosis.

The foregoing data thus demonstrate a correlation between increased CD36 expression and hyperglycemia in atherosclerotic vascular lesions, which thus offers potential opportunity and advantage to use CD36 as a potential molecular maker of atherosclerosis.

6. Leptin:

Leptin plays an important role in regulating energy expenditure in response to food intake. Leptin is an important adipocytokine of adipose tissues, which further contain low and medium molecular weight proteins like adiponectin, tumor necrosis factor-alpha (TNF-alpha), interleukin-6 (IL-6), resistin, plasminogen-activating inhibitor-I (PAI-1), and angiotensinogen. Together these cytokines play an important role in the adipose tissue physiology and are believed to be a link between obesity, insulin resistance and endothelial dysfunction.

In vivo gene expression of leptin, Fatty acid translocase (FAT/CD36), PPAR-gamma2, Uncoupling protein (UCP)-2, UCP-3, and TNF-alpha in subcutaneous adipose tissue is regulated by circulating lipids independent of insulin. Hence prolonged hyperlipidemia may contribute to increased fat metabolism and storage as a result of the increased expression of these proteins. [Nisoli E et al.; Diabetes. 2000 March; 49(3):319-24].

7. Oxidized LDL:

LDL cholesterol which is known as bad cholesterol becomes more dangerous when it is oxidized. Oxidized LDL can produce inflammation in arteries that supply blood to various organs and tissues. This leads to Atherosclerosis and increases the risk of heart attack or stroke.

Holvoet et al showed for the first time that the metabolic syndrome is associated with a higher fraction of oxidized LDL and thus with higher levels of circulating oxidized LDL. In this study, oxidized LDL was measured with a monoclonal antibody-based enzyme-linked immunosorbent assay. They proved that increased concentration of oxidized LDL was associated with increased incidence of metabolic syndrome overall, as well as its components of abdominal obesity, hyperglycemia, and hypertriglyceridemia. [Holvoet P et al., JAMA. 2008 May 21; 299(19):2287-93.].

A study conducted on women with polycystic ovarian syndrome (PCOS) manifested that elevated OxLDL and a direct relation of ApoE (Apoliprotein) and nonesterified fatty acids with insulin resistance could possibly have been the increase risk for premature atherosclerosis in these women.

8. Monocyte Chemotactic Protein (MCP-1):

Monocyte chemotactic protein-1 (MCP-1), a member of the small inducible gene (SIG) family, plays a role in the recruitment of monocytes to sites of injury and infection. MCP-1 has also been called small inducible cytokine A2 (SCYA2) and monocyte chemotactic and activating factor (MCAF). MCP-1 has been found in the joints of people with rheumatoid arthritis, which may serve to recruit macrophages and perpetuate the inflammation in the joints. MCP-1 has also been found elevated in the urine of people with lupus as a warning sign for inflammation of the kidney. [http://www.medterms.com/script/main/art.asp?articlekey=33740].

Recently, MCP-1 has been reported to be a novel adipocytokine involved in the development of obesity-associated insulin resistance and atherosclerosis. [Kawada T, et. al., Asia Pac J Clin Nutr. 2008; 17 (1):126-30]. MCP-1 along with a number of other adipokines, including leptin, adiponectin, tumour necrosis factor alpha, etc. is linked to inflammation and the inflammatory response. Obesity is characterized by a state of chronic mild inflammation, with raised circulating levels of inflammatory markers and the expression. This elevated production of inflammation-related adipokines is increasingly considered to be important in the development of diseases linked to obesity, particularly Type II diabetes and the metabolic syndrome. [Trayhurn P. and Wood I. S., Biochem Soc Trans. 2005; 33(Pt 5):1078-81].

9. Fatty-Acid-Binding Protein (aP2/FABP4):

FABPs are molecular chaperones linked to metabolic and inflammatory pathways. Different members of the FABP family exhibit unique patterns of tissue expression/distribution and are expressed most abundantly in tissues involved in active lipid metabolism. FABPs play numerous functions. As lipid chaperones, for example, FABPs may actively facilitate the transport of lipids to specific compartments in the cell, such as to the lipid droplet for storage; to the endoplasmic reticulum for signaling, trafficking and membrane synthesis; to the mitochondria or peroxisome for oxidation [Masato, F et al, Nature Reviews/Drug Discovery, Vol. 7: 489-503, 2008]. A-FABP is Fatty Acid Binding Protein prominently expressed in mature adipocytes and macrophages. It is more familiarly known as FABP-4 and aP2. Adipocytes, however, express significantly higher levels (approximately 10000-fold) of A-FABP than macrophages, upon their differentiation from pre-adipocytes and monocytes respectively.

A-FABP is abundantly present in human serum and it may play a central role in the development of major components of the metabolic syndrome such as obesity, type 2 diabetes and cardiovascular diseases, through its distinct actions in adipocytes and macrophages and its ability to integrate metabolic and inflammatory responses [Masato, F et al, Nature Reviews/Drug Discovery, Vol. 7: 489-503, 2008]. The aP2 expressed in adipocytes regulates systemic glucose and lipid metabolism.

Blocking aP2 function is a novel approach to therapeutic strategy for the treatment of obesity, tracking heart disease, Metabolic Syndrome and other components of Metabolic Syndrome.

10. β3-Adrenergic Receptor (β3AR):

The body's adrenergic system plays a major part in regulating energy expenditure and lipolysis. In this process catecholamines mobilize energy-rich lipids by stimulating lipolysis in fat cells and thermogenesis in brown adipose tissue and skeletal muscle. The β3AR is the principal receptor mediating catecholamine-stimulated thermogenesis in brown adipose tissue, which in humans is distributed about the great vessels in the thorax and abdomen [Thomas, G N, International Journal of Obesity, 545-551, 24, 2000]. The β3AR is also important in mediating the stimulation of lipolysis by catecholamines in the white fat cells of several species, including humans. The brown adipose tissue differs from white adipose tissue in that it has large numbers of mitochondria containing a so-called uncoupling protein, which can stimulate oxidative phosphorylation and thereby increase the metabolic rate. The role of brown adipose tissue is to oxidize lipids to produce heat and rid the body of excess fat. White adipose tissue, which includes subcutaneous and visceral adipose tissue, is much more abundant. It serves to store fat, which can be mobilized by lipolysis to generate free fatty acids for use by other tissues.

Selective agonists of β3ARs are potentially useful in treating obesity because they could enhance energy expenditure with few β1- or β2-adrenergic side effects. A number of β3-adrenergic agonists have been developed and tested experimentally. Hence the treatment with β3-selective agonists can markedly increase energy expenditure and decreases obesity.

11. Perilipin:

Perilipin is a protein that forms a coating around the lipid droplets in the fat-storing cells in adipose tissue, called adipocytes. Perilipin acts as a protective coating against body's natural lipases, such as hormone-sensitive lipase, that break triglycerides into glycerol and free fatty acids by a process called lipolysis.

In a study, it was suggested that the family of Perilipin [PLIN], adipophilin and TIP47 proteins may play key roles in obesity. PLIN is a candidate gene for obesity risk in humans as well as a modulator of dietary response to therapies aimed to reduce body weight and risk of metabolic syndrome. [Tai E S et al; Curr Opin Lipidol. 2007; 18(2): 152-6].

Following β-adrenergic receptor activation, protein kinase A (PKA) hyperphosphorylates perilipin localized at the surface of the lipid droplet. Phosphorylated perilipin changes conformation and translocate away from the lipid droplet, exposing the stored lipids to hormone-sensitive lipase-mediated hydrolysis of triglycerides (lipolysis) to release nonesterified fatty acids (NEFA). Perilipin is thus an important regulator of lipid storage, lipolysis and energy balance. Perilipin expression is elevated in obese animals and humans. Studies manifested a significant positive relationship between perilipin expression and obesity (P<0.01, perilipin mRNA vs. percent body fat). Because of the potential importance of adipocyte lipolysis to obesity and insulin resistance, perilipin is an important target for developing anti-obesity drugs. Agents that inactivate or inhibit perilipin may find application as potential anti-obesity medications.

12. Adiponectin:

Adiponectin is an important adipokine and it was proved that low levels of adiponectin are associated with disease states such as obesity, diabetes and cardiovascular disease. Administration of adiponectin was proved to be beneficial in animal models of diabetes, obesity and atherosclerosis.

Adiponectin level in blood is decreased in obesity and it is considered to have antidiabetic and antiatherogenic effect, whereas increased leptin level in blood in obesity is associated with regulation of appetite, energy expenditure, lipids and carbohydrates metabolism, cellular differentiation. In a study carried out on 80 patients (43 female and 37 male) from Obese families, the fasting level of leptin (Elisa), adiponectin (Elisa) and von Willebrand factor (Elisa) lipidogram were performed. It was found that the leptin to adiponectin ratio (Lep/AdipoR) in the blood was significantly higher in obese patients in comparison to people with normal BMI. Relative Operating Characteristic (ROC) showed that with reference to obesity Lep/AdipoR had the highest discriminatory value. The estimation of Lep/AdipoR can be used as additional index in evaluation of obesity complications such as insulin resistance and endothelial dysfunction.

It was also proved that high plasma concentrations of adiponectin are associated with lower risk of Myocardial Infarction in men. [Pischon T et al., JAMA. 2004 Apr. 14; 291(14):1730-7]. Hence the phytochemical extracts or fractions or compounds that enhance the adiponectin levels can have beneficial effects on obesity, diabetes, cardiovascular system and metabolic syndrome and other disease components associated with metabolic syndrome.

13. Protein Tyrosine Phosphatase 1B (PTP-1B):

Resistance to the hormone insulin is the hallmark of type 2 diabetes and obesity. Protein tyrosine phosphatase 1B (PTP-1B) is regarded as a negative regulator of insulin signal transduction in insulin sensitive cells such as adipocytes, muscle cells and hepatocytes. In insulin resistant diabetes and obesity, the PTB-1B is over expressed and its enzyme activity is increased. Over expression of PTP1B decreases insulin receptor and IRS-1 Phosphorylation and thus produces insulin resistance (Theodore O. J., et al., Nature Reviews Drug Discovery, 1; 696-709, 2002; Carol L. V., et. al., J. Biol. Chem. 275: 18318-18326, 2000.). Therefore, agent(s) providing PTP-1B inhibition has become an emerging therapeutic promise to patients with at-risk obesity and or type-2 diabetes.

14. Adipogenesis:

Adipogenesis is the differentiation and proliferation of pre-adipocytes into major adipocytes or fat cells and it has been one of the most intensely studied models of cellular differentiation. In the adipogenesis process, proliferation of preadipocytes or precursor fat cells is followed by the differentiation of these cells to the mature adipocyte phenotype. The nuclear receptor PPAR γ is expressed predominantly in adipose tissue, where it is known to play a critical role in adipocyte differentiation and fat deposition. Many drugs in the market for the treatment of diabetes type-II, however involve over expression of PPAR γ and promotion of adipogenesis.

Adipocytes secrete proteins exhibiting either beneficial (leptin, adiponectin) or deleterious effects (angiotensinogen). A disturbance in the balance between these various secreted factors, in association with the effect of secretory products from macrophages (cytokines), leads to the development of metabolic syndrome.

15. Lipolysis:

Lipolysis is the breakdown of stored lipid in adipocytes. β3-Adrenoreceptor agonists can stimulate lipolysis in the white adipose tissue and thermogenesis in the brown adipose tissue. The phytochemical agents having the lipolysis activity could be useful in the treatment of obesity, metabolic syndrome and other metabolic disorders. Adipose tissue lipolysis is the catabolic process leading to the breakdown of triglycerides stored in fat cells and release of fatty acids and glycerol. The proteins involved in the lipolytic process constitute drug targets for the treatment of obesity and the metabolic syndrome.

16. Alpha-Amylase (α-Amylase):

α-amylase is an enzyme that converts complex carbohydrates such as starch into sugar. Starches cannot be absorbed unless they are first broken down by the digestive enzyme amylase and other secondary enzymes. When carbohydrates are consumed, enzymes in the digestive tract break these large molecules down into smaller sugar molecules, which are absorbed through the intestine. Recently, starch blockers have been shown to be effective treatments for the control of obesity. Amylase inhibitors thus have gastrointestinal and metabolic effects that may aid in the treatment of diabetes and obesity.

Plants also use α-amylase inhibitors as a defence strategy. These inhibitors impede the digestive action of α-amylases and proteinases in the insect gut, thereby acting as insect anti-feedants. The alpha-amylase inhibitors isolated from the plants may be used as starch blockers to considerably reduce the quantity of glucose originating from the starches present in the diet, and reduces the appetite after repeated administration.

17. Alpha-Glucosidase (α-Glucosidase):

Alpha-glucosidase is an enzyme that catalyses the degradation of complex carbohydrates into glucose. As such its action is similar to α-amylase. By inhibiting this enzyme, carbohydrates are not broken down as efficiently and glucose absorption from intestine is delayed, resulting in a slower and lower rise in blood glucose throughout the day, especially right after meals. A few α-glucosidase inhibitors, such as acarbose, miglitol and voglibose are oral antidiabetic drugs commercial available in the market for the treatment and control of diabetes mellitus type 2. Plant extracts, fractions or pure compounds having α-glucosidase inhibition may thus be useful to establish greater glycemic control over hyperglycemia in diabetes mellitus type 2, particularly with regard to postprandial hyperglycemia.

Metabolic Syndrome is recognized as an important disease which can be single or can be a set of diseased conditions, such as obesity, diabetes and atherosclerosis and if it is left untreated leads to several complications. Even though several classes of drugs are available in the market for the treatment of different components of Metabolic Syndrome and many of them are associated with a number of side effects, very few medicines are available to treat Metabolic Syndrome and none of them are comprehensive in addressing all the associated diseases. Hence there exists a great medicinal need for developing the protection and treatment against metabolic syndrome, obesity, diabetes and atherosclerosis especially using safe and beneficial natural compounds.

One of the key developments in obesity research in the past decades has been the general recognition that obesity is a chronic low level inflammation. The link between obesity and inflammation has been obvious from the increased plasma levels of several inflammatory markers including cytokines (TNFα, IL-6) and acute phase proteins like C-reactive protein (CRP) in obese individuals (Stienstra R., et. al., 2007, article ID 95974). Thus obesity, diabetes and atherosclerosis as well as other components of the metabolic syndrome have been casually linked to inflammation. It has also been theorized in recent years that chronic, low-grade tissue inflammation related to obesity contributes to insulin resistance, the major cause of Type 2 diabetes (Science News, *Science Daily*, U.S., Nov. 7, 2007).

The research activity in the area of metabolic disorders has been a high priority target for numerous scientists around the world, with a special interest in finding alternative solutions, especially those based on products of plant origin, as the plant derived products are considered to be natural and safe, in contrast to the commercial drugs of synthetic origin. Keeping this in mind and in conjunction with the urgent need for the prevention, control and treatment of metabolic syndrome, obesity, diabetes, atherosclerosis and endothelial dysfunction and other metabolic disorders, the inventors have conducted extensive research investigation involving several in vitro and in vivo experiments on several plant extracts, fractions and pure compounds and accidentally found that administration of the extracts, fractions, active compounds derived from the herb *Sphaeranthus indicus* in a therapeutically effective amount in cell based studies potently ameliorated metabolic processes which include inhibition of adipogenesis and also promotion of adipolysis (lipolysis). The inventors also found unexpectedly that the administration of one or more of the ingredient(s) selected from the extracts, fractions, active compounds derived from the herb *Sphaeranthus indicus* in a therapeutically effective amount in cell based studies potently ameliorated the levels of certain biomarker molecules or biological proteins that are altered during metabolic syndrome, obesity, diabetes, atherosclerosis, endothelial dysfunction and other disease conditions associated with metabolic syndrome.

The inhibition of lipid accumulation in differentiated adipocytes exhibited by the ethyl actate extract (LI/DD-II/054A/01) of the flower heads of *Sphaeranthus indicus* was assessed in 3T3-L1 mouse pre-adipocyte cells. The inhibition of fat accumulation in the treated cells was compared with the mock treated differentiated adipocytes and percentage inhibition was measured. Unexpectedly, the ethyl acetate extract (LI/DD-II/054A/01) of *Sphaeranthus indicus* significantly inhibited the adipogenesis 65.9% inhibition of lipid accumulation at 10 µg/ml as summarized in Table 1.

Similarly, the pro-lipolytic activity of the ethyl actate extract (LI/DD-II/054A/01) of *Sphaeranthus indicus* was assessed in differentiated/mature adipocytes using 3T3-L1 pre-adipocyte cells. The lipolytic activity was assessed in mature adipocytes by measuring free glycerol secreted into the culture medium as per the procedure of Adipolysis Assay Kit (Chemicon International, USA). The percentage increase in glycerol concentration in the sample solutions compared to the control containing the known concentrations of glycerol corresponds to the percentage acceleration of lipolysis exhibited by extract LI/DD-II/054A/01 of *Sphaeranthus indicus*. Unexpectedly, LI/DD-II/054A/01 showed moderate enhancement of lipolysis/adipolysis with 26.7% increase in lipolysis at 25 µg/ml as summarized in Table 2.

Bio-assay guided purification was undertaken on LI/DD-II/054A/01 to identify the active compound and it was found accidentally that 7-α-hydroxy-4,11(13)-eudesmadien-12,6-olide also known as 7-hydroxyfrullanolide (LI054A01; 1) was found to be responsible for the activity. The active compound 7-α-hydroxy-4,11(13)-eudesmadien-12,6-olide also known as 7-hydroxyfrullanolide (LI054A01) exhibited superior activity and showed 68.7% inhibition of lipid accumulation (adipogenesis) at 0.5 µg/ml concentration and 47.8% increase lipolysis at 5 µg/ml concentration as summarized in Tables 1 and 2.

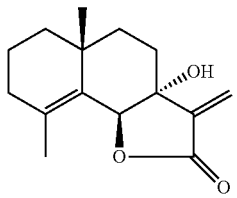

7-Hydroxyfrullanolide

It was also found surprisingly that the ethyl actate extract (LI/DD-II/054A/01) of *Sphaeranthus indicus* possessed potent Matrix Metalloproteinase-1 (MMP-1) inhibition activity (FIG. 1) in PMA induced A2058 human melanoma cells. Phorbol myristate acetate (PMA) is a potent known intracellular oxidative stress-inducing agent. In cardiovascular manifestation, such as atherosclerosis, over production of oxidative stress markers is a critical factor. In addition, LI/DD-II/054A/01 also showed potent Matrix Metalloproteinase-3 (MMP-3) inhibition (FIG. 2) in Interleukin-1β induced A549 human lung tumor cells. In atherosclerosis, over production of pro-inflammatory proteases such as MMP-3, MMP-9, MMP-13 under the influence of pro-inflammatory cytokines such as IL-1β is important crucial for development and progression of atherosclerotic lesions and aneurysm formation The inventors have then evaluated the modulation of metabolic biomarkers those are primarily responsible for the adipogenesis processes, insulin resistance in type 2 diabetes, obesity, metabolic syndrome and other metabolic disorders such as Peroxisome proliferator-activated receptor gamma (PPARγ), CD36, adipocyte fatty acid binding protein 4 (FABP4 or aP2), Perilipin, and beta-3 Adrenergic Receptor (β3AR) during adipogenesis process in 3T3-L1 adipocytes by ethyl actate extract (LI/DD-II/054A/01) of *Sphaeranthus indicus* and 7-hydroxyfrullanolide (LI054A01) using an immunoblot assay. The mouse pre-adipocyte 3T3-L1 cells under maintenance in Dulbecco's Modified Eagle's Medium (DMEM) were pre-treated with different concentrations of LI/DD-II/054A/01 for 2 h, followed by addition of differentiation medium containing 500 nM insulin, 1.0 µM dexamethasone, and 0.5 mM isobutylmethylxanthine (IBMX) for 48 h. Thereafter, cells were further incubated with post differentiation medium (DMEM containing 100 nM insulin) in presence or absence of LI/DD-II/054A/01 or LI054A01 for further 8 days. Finally, the cells were processed and lysed with the lysis buffer. The protein extracts were evaluated by immunoblot assay, and the immuno-reactive bands were developed with West-pico chemiluminescent substrate and the blot images were captured in a Kodak Image Station, normalized with expression of actin.

It was found surprisingly that both the ethyl acetate extract (LI/DD-II/054A/01) and the active compound 7-hydroxyfrullanolide (LI054A01) potently ameliorated the levels of several adipocyte differentiation markers such as Peroxisome proliferator-activated receptor gamma (PPARγ), CD36, Fatty Acid Binding Protein 4 (aP2/FABP4) and intracellular lipid droplet surface associated protein (perilipin) (FIG. 3) in a dose dependent manner. The down regulation of several marker proteins in LI/DD-II/054A/01 treated adipocytes suggests that the ethyl acetate extract of *Sphaeranthus indicus* exerts multiple beneficial roles in controlling the adipogenic differentiation process; by (1) inhibiting cellular differentiation by down regulating PPAR, which is a nuclear receptor protein that functions as a transcription factor for regulation of cellular differentiation, development and metabolism. (2) restricting cholesterol ester uptake by inhibiting CD36, which is a class B scavenger receptor involved in lipid uptake, (3) decreasing intracellular adiposity and intracellular lipid transport by reducing FABP4/aP2 level, which acts as a transport protein for long chain fatty acids. Moreover, down regulation of perilipin protein in LI/DD-II/054A/01 treated adipocytes strongly indicate the reduced fat store in the cytoplasm. Perilipin is a protein that coats lipid droplets in adipocytes. It offers protection from the action of hormone-sensitive lipase, which breaks triglycerides into glycerol and free fatty acids for use in metabolism or lipolysis. Therefore it is indicative that ethyl acetate extract of *Sphaeranthus indicus* provides such a state where the stored lipids are more susceptible to enzymatic break down into glycerol and free fatty acids by thinning the perilipin coat around the lipid filled vesicles.

Figure 3:
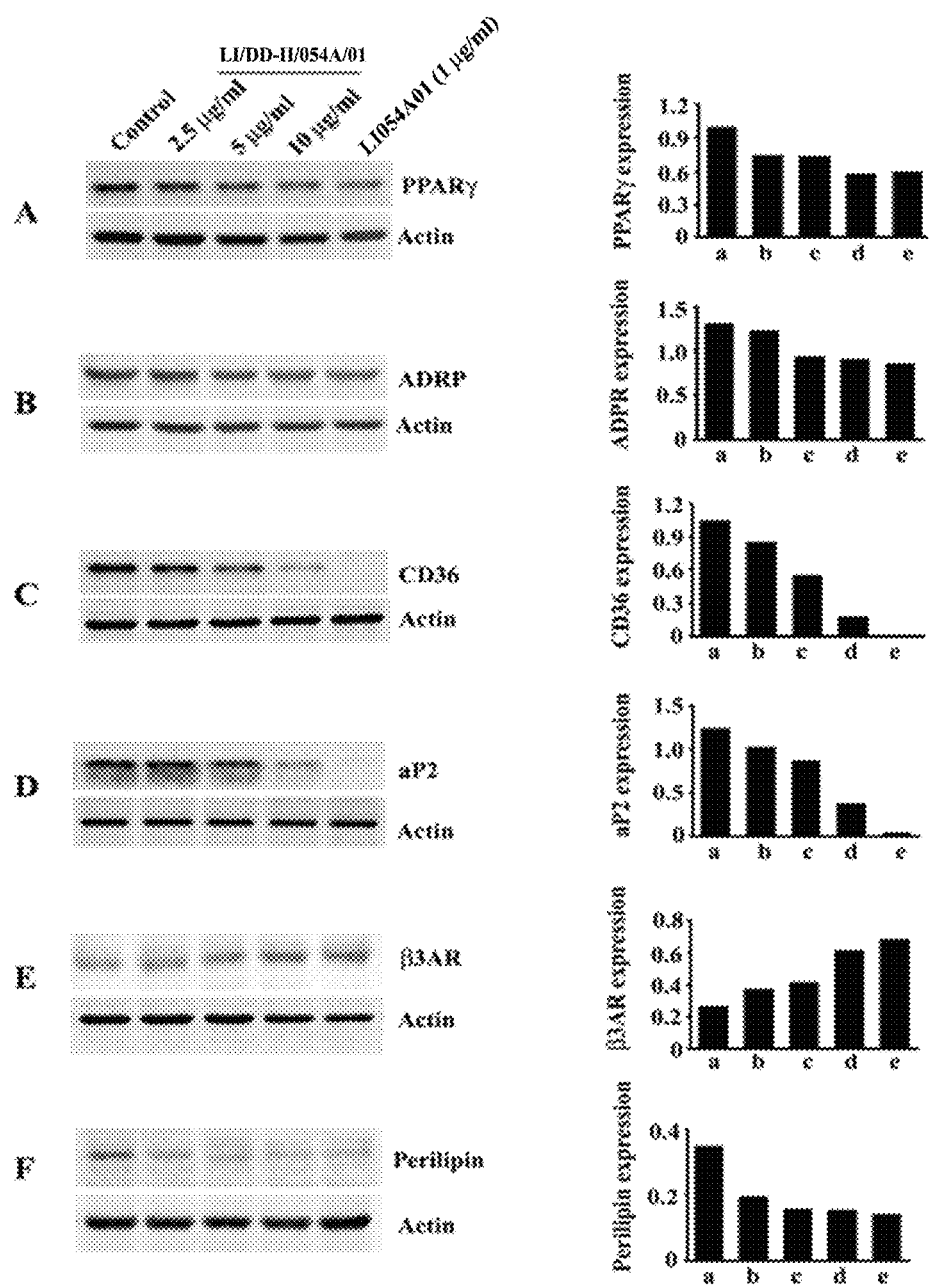
FIG. 3: Illustrates the modulating of marker proteins of Adipogenesis and lipolysis processes in 3T3-L1 adipocytes by *Sphaeranthus indicus* ethyl acetate extract (LI/DD-II/054A/01) and 7-hydroxyfrullanolide (LI054A01). Representative immuno blots indicate down-regulation of various marker proteins such as PPARγ (A), ADRP (B), CD36 (C), aP2 (D), β3AR(E) and perilipin (F). The 3T3-L1 mouse pre-adipocytes were allowed to differentiate in absence or presence of various concentrations of LI/DD-II/054A/01 or LI054A01 as indicated. Vehicle control cultures received similar concentrations of DMSO only. Expression of actin protein was evaluated in each blot as the internal control. Expression of each protein was measured densitometrically and normalized with actin expression. The comparative levels are represented as bar diagrams (side panels).

In addition, the beta-3 Adrenergic Receptor (β3AR) expression/production in 3T3-L1 adipocytes was significantly enhanced by LI/DD-II/054A/01 in a dose dependent manner as shown in FIG. 3. This is indicative of weight loss through increasing energy expenditure via increasing intracellular cAMP and activation of the mitochondrial uncoupling protein 1 in the adipose tissue.

In macrophages, CD36 is a scavenger receptor that mediates uptake of oxidized low-density lipoprotein (OxLDL) and subsequent foam-cell development. Therefore, increased level of CD36 in macrophages has been considered as a predictive marker for development of atherosclerosis. Inhibition of CD36 protein expression in high glucose induced J774 macrophage cells in presence or absence of LI/DD-II/054A/01 and LI054A01 was evaluated using immunoblot assay. Briefly, equal amount of cell lysates protein obtained after treating the cells with LI/DD-II/054A/01 or LI054A01 was resolved in 7.5% SDS-PAGE; thereafter, the proteins were transferred to nitrocellulose membrane. After blocking the non-specific sites, the membrane was incubated with CD36 antibody (R&D Systems, Minneapolis, Minn.). Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The results are summarized in FIG. 3. The representative immunoblot image indicated that LI/DD-II/054A/01 dose dependently inhibited the CD36 protein expression in high glucose induced J774 macrophage cells. The active compound LI054A01 however has shown 10 times better inhibition of CD36 compared to that shown by LI/DD-II/054A/01. This unexpected observation also provides support in favor of anti-atherosclerotic properties of the extracts and compounds of *Sphaeranthus indicus*.

Figure 7:
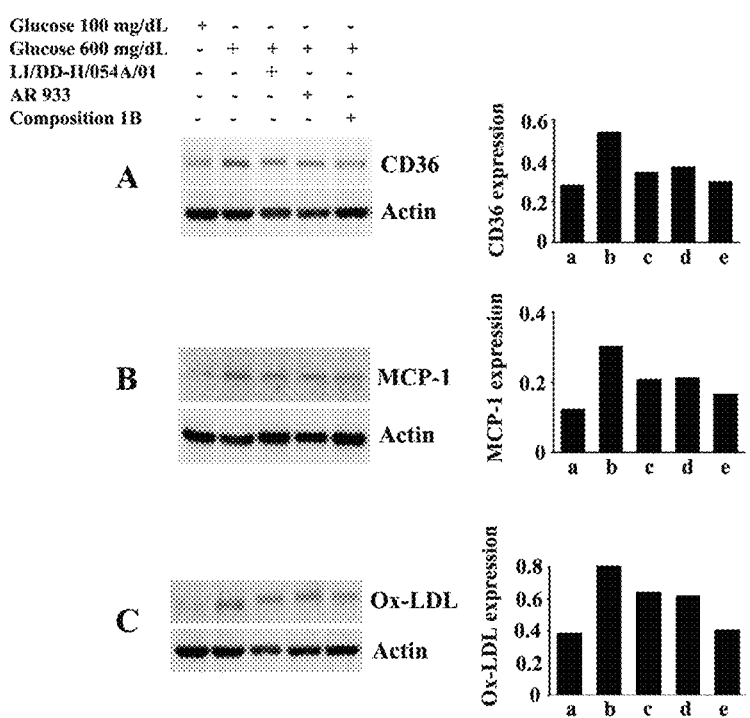
FIG. 7: Representative immunoblots showing down-regulation of atherosclerotic markers in high glucose induced macrophage cells treated with either *Sphaeranthus indicus* ethyl acetate extract (LI/DD-II/054A/01) or *Garcinia mangostana* methanol extract (AR 933) or composition 1B. Immuno blots show down regulation of CD36 (A), MCP-1 (B) and Ox-LDL (C) protein expression. Expression of actin protein is considered as the loading control. Bar diagrams in respective panels show the normalized protein expression. Bars represent expression levels for a, Glucose 100 mg/dL; b, Glucose 600 mg/dL; c, LI/DD-II/054A/01 (5 µg/ml); d, AR 933 (5 µg/ml), and e, composition 1B (5 µg/ml).

It is also interesting to note that the ethyl acetate extract (LI/DD-II/054A/01) also potently inhibited Monocyte Chemotactic protein-1 (MCP-1) and oxidized LDL in high glucose induced macrophage cells. These markers are critically important for differentiation into foam cells to develop atherosclerotic plaque and are considered as potential biological markers for development and progression of atherosclerosis (FIG. 7).

Figure 8:
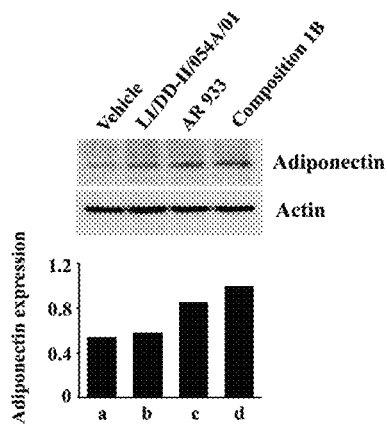
FIG. 8: Representative immunoblot showing over expression of adiponectin protein in 3T3-L1 adipocytes treated with 5 µg/ml of either LI/DD-II/054A/01 or AR 933 or composition 1B treated. Protein expressions were densitometrically analyzed and normalized with the actin expression. Bar diagram in each panel shows normalized protein expressions in arbitrary units. In bar diagrams, the bars represent protein expressions in cells treated with vehicle control (a), LI/DD-II/054A/01 (b), AR 933 (c) and composition 1B (d).

Similarly, the modulation of adiponectin protein by ethyl acetate extract (LI/DD-II/054A/01) of *Sphaeranthus indicus* in 3T3-L1 adipocytes was evaluated in Western immunoblot assay. The cell culture, treatment protocol and immunoblot assay methodology were as per the standard protocol and as briefly described above for metabolic markers. The extract LI/DD-II/054A/01 also showed moderate upregulation of adiponectin protein expression in 3T3-L1 mature adipocytes as depicted in FIG. 8. Adiponectin is a hormone secreted by adipocytes. It reduces intracellular triglyceride content and up-regulates glucose uptake by potentiating insulin signaling, thus it provides protection from both adipogenicity and from developing insulin resistant diabetes or type 2 diabetes. Therefore, our finding indicates that the extracts of *Sphaeranthus indicus* provides protection against developing obesity, insulin resistant or Type 2 diabetes and also helps in attenuating endothelial dysfunction disorders as well. These extracts can thus be useful in the prevention, treatment and control of above metabolic disorders.

Figure 9:
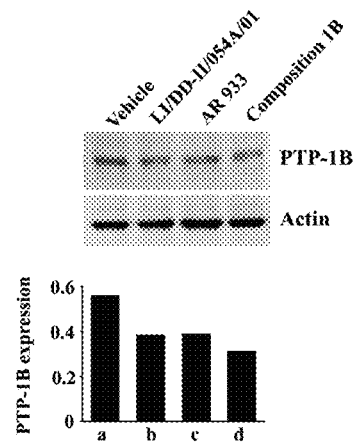
FIG. 9: Representative immunoblot showing down regulation of PTP-1B protein expression in 3T3-L1 adipocytes treated with 5 µg/ml of either LI/DD-II/054A/01 or AR 933 or composition 1B. Protein expressions were densitometrically analyzed and normalized with the actin expression. Bar diagram in each panel shows normalized protein expressions in arbitrary units. In bar diagram, the bars represent protein expressions in cells treated with vehicle control (a), LI/DD-II/054A/01 (b), AR 933 (c) and composition 1B (d).

The effect of *Sphaeranthus indicus* ethyl acetate extract (LI/DD-II/054A/01) on insulin sensitivity was evaluated by studying the modulation of Protein Tyrosine Phosphatase-1B (PTP-1B) activity in 3T3-L1 preadipocytes by LI/DD-II/054A/01. The 3T3-L1 preadipocytes were cultured in Dulbecco's Modified Eagle's Medium (DMEM) as per standard protocol and treated with LI/DD-II/054A/01 for 48 h. The cells were lysed with cell lysis buffer and the cell lysates were clarified at 14,000×g for 5 min at 4° C. The PTP-1B activity was estimated by using substrate reagent containing 10 mM 4-nitrophenylphosphate (pNPP, Sigma Chemical Co., MO, USA) following the standard protocol and the color reaction was read in a microplate ELISA reader (BioRad, USA). The results showed unexpectedly that LI/DD-II/054A/01 could be a potent inhibitor of PTP-1B activity in 3T3-L1 preadipocytes (FIG. 9).

Protein-tyrosine phosphatase (PTP)-1B acts as a physiological negative regulator of insulin signaling by dephosphorylating the phosphotyrosine residues of the insulin receptor and Insulin receptor-substrate complex 1 (IRS-1). Silencing of PTP-1B gene in a prior animal study astonishingly provided resistance from developing type 2 diabetes. Therefore, inhibition of PTP-1B has recently been emerged as a potential target to treat type 2 diabetes. Interestingly, LI/DD-II/054A/01 in the present invention exhibited significant inhibition of PTP-1B activity in adipocytes (FIG. 9). This observation thus indicates that the extracts of *Sphaeranthus indicus* can also be used as a potential therapeutic intervention to treat type 2 diabetes.

It was quite unexpected and surprising to see that a single ingredient derived from *Sphaeranthus indicus* could be able to modulate the marker proteins related to many disease conditions associated with metabolic syndrome and other metabolic disorders. This unexpected result suggests that *Sphaeranthus indicus* derived extract(s), fraction(s) and compound(s) could be a potential therapeutic agent to prevent, treat and control metabolic syndrome, obesity, diabetes, atherosclerosis, endothelial dysfunction, chronic kidney disease (CKD) and other metabolic disorders in animals and humans.

Figure 10A:
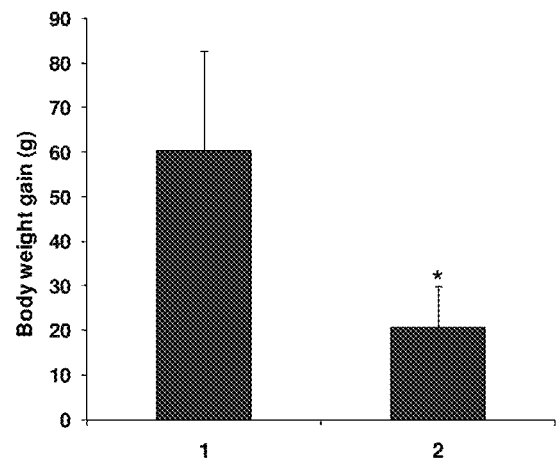
FIG. 10A: Bar diagrammatic representation of body mean weight gain in HFD induced metabolic syndrome model of SD rats supplemented without (1) or with (2) LI/DD-II/054A/01 from week-1 to week-8 of treatment. Each bar represents mean±SD, *p<0.05.
Figure 10B:
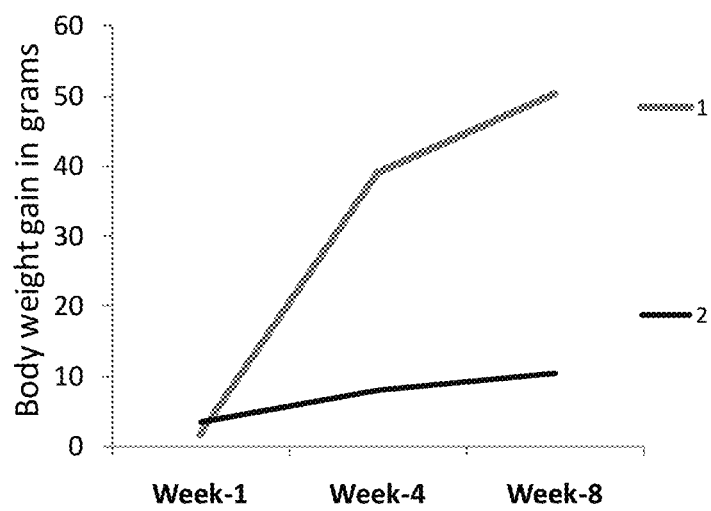
FIG. 10B: Line diagrammatic representations of body weight in diet induced metabolic syndrome model of SD rats supplemented with (2) or without (1) LI/DD-II/054A/01. Each line indicates change in mean body weight gain during eight-week treatment period.

The potent anti-metabolic syndrome effect shown by LI/DD-II/054A/01 in vitro models was further evaluated in an in vivo model of metabolic syndrome. Metabolic syndrome condition was experimentally induced in male Sprague Dawley rats by feeding the rats with high fat, high cholesterol, high salt and high sucrose diet for eight weeks. After eight weeks of induction period, the rats were randomly divided into two groups with six animals in each group and the treatment group animals were supplemented orally with 250 mg/kg body weight of LI/DD-II/054A/01 in 10 mL of 0.5% CMC in water for further 8 weeks. The control group of animals received only the vehicle (10 mL/kg of 0.5% CMC in water) during this period. Body weight of individual animal was recorded weekly for the entire duration of the study. Mean body weights for the treatment group and control group were determined. The body weight gain was calculated at the end of 1st week, 4th week and 8th week after initiation of treatment in comparison to initial body weight. LI/DD-II/054A/01 at a dose of 250 mg/kg exhibited highly potent and statistically significant ($p<0.01$) reduction in body weight gain (66.04%) in comparison to control group. The results of body weight gain in the treatment group and control group are summarized in FIGS. 10A and 10B.

Figure 11:
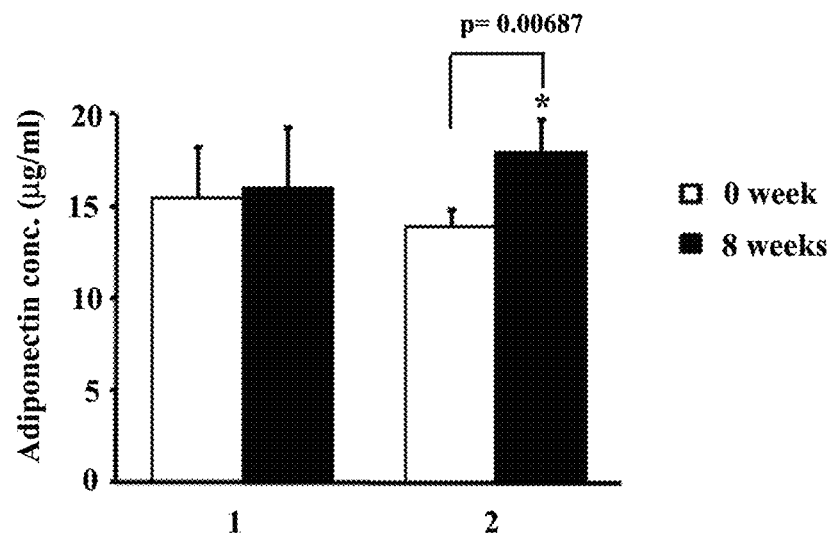
FIG. 11: Bar diagrammatic representation of increase in serum adiponectin concentration in diet induced metabolic syndrome model of Sprague Dawley rats. Each bar indicates mean±SD of serum adiponectin concentration at 0 day and after 56 days of treatment with either vehicle (1) or LI/DD-II/054A/01 (2) as indicated in the diagram. N=6, * indicates statistical significance (t-test, 8 weeks vs. 0 week).

Assessment of serum adiponectin: Adiponectin is a protein hormone exclusively secreted from the adipose tissue, which modulates number of metabolic processes including glucose homeostasis and lipid metabolism. The circulatory adiponectin concentration is inversely correlated with body fat. Low level of adiponectin is related with obesity, cardiovascular disorder and insulin resistance. Therefore, this protein hormone has been established as a promising marker of metabolic syndrome and disease conditions associated with metabolic syndrome. The serum adiponectin concentration in the treatment and control groups of animals was assessed using double antibody based sandwich rat adiponectin ELISA kit. The data revealed that daily supplementation of LI/DD-II/054A/01 at 250 mg/kg body weight for 8 weeks resulted in significant ($p=0.00618$) improvement in serum adiponectin concentration, when compared to the baseline as summarized in FIG. 11. The control group, however, did not show improvement in serum adiponectin concentration. Hence LI/DD-II/054A/01 has potential benefit in alleviating the symptoms such as obesity, cardiovascular disorders, insulin resistant type-II diabetes, metabolic syndrome and other related disorders of metabolic syndrome.

Supplementation of LI/DD-II/054A/01 at 250 mg/kg resulted in improvement in fat profile with 15.3, 12.7 and 22.9 percentage reductions respectively in serum cholesterol, LDL and triglycerides. This is well corroborated with its efficacy observed in improvement of adiponectin levels.

Figure 12:
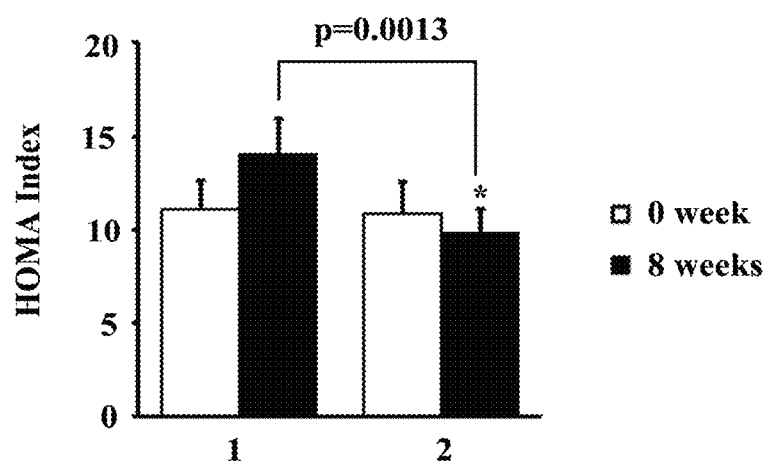
FIG. 12: Bar diagrammatic representation of reduction of HOMA Index in LI/DD-II/054A/01 supplemented metabolic syndrome model of Sprague Dawley rats. Each bar indicates mean±SD of HOMA Index (arbitrary units) at 0 week and at 8 weeks of supplement with either vehicle (1) or 250 mg/kg of LI/DD-II/054A/01 (2). N=6; * indicates statistical significance (t-test, LI/DD-II/054A/01 group vs. control at 8 weeks).

Homeostasis Model Assessment (HOMA):

The HOMA index was calculated based on serum insulin and glucose levels using the formula: Fasting insulin concentration (μU/mL)×Fasting glucose concentration (mmol/L)/22.5. The data presented in FIG. 12 manifested that compared to the control group, supplementation of a daily dose of 250 mg/kg of LI/DD-II/054A/01 for 8-weeks resulted in significant reduction of HOMA index. The Homeostatic Model Assessment (HOMA) is widely considered as a measure of insulin resistance and beta cell function in clinical research. The data indicates that LI/DD-II/054A/01 can be a therapeutic agent to improve insulin sensitivity and β-cell function.

Based on the present animal study, it is obvious that LI/DD-II/054A/01 not only reduces obesity but also ameliorates various symptoms of the metabolic syndrome including body weight gain, visceral and organ fat deposition and improves lipid profile, glucose homeostasis, β-cell function etc. The reduction in body weight gain obtained by LI/DD-II/054A/01 treatment was statistically significant. Additionally, fat tissue weight was also significantly reduced in LI/DD-II/054A/01 treatment group. In conclusion, LI/DD-II/054A/01 can be effective agent for the treatment of obesity, metabolic syndrome and other related metabolic disorders.

Figure 5:
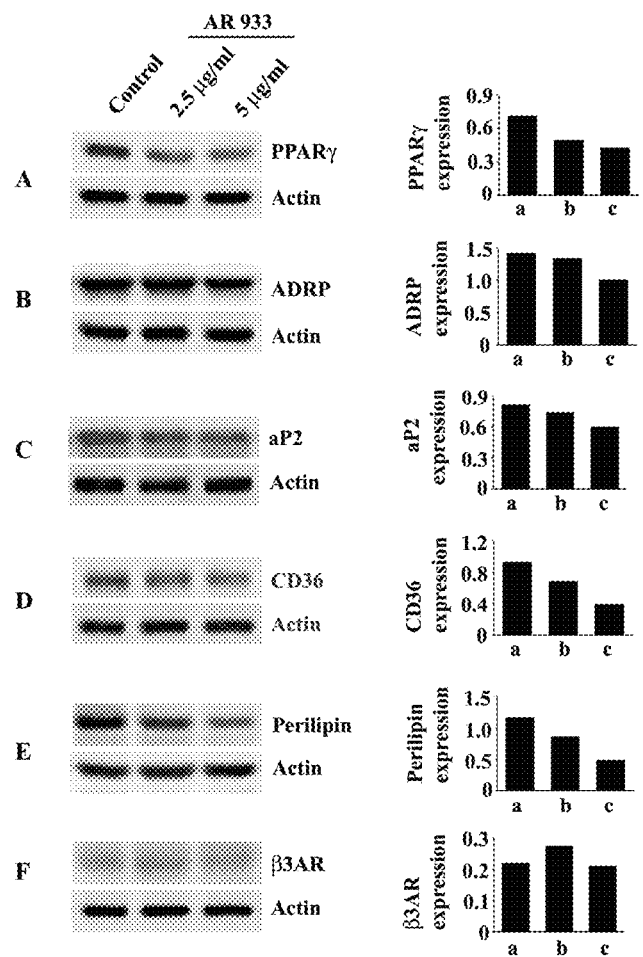
FIG. 5: Representative immuno blots showing the modulations of PPAR (A), ADRP (B), aP2 (C), CD36 (D), perilipin (E) and β3AR (F) protein expressions in 3T3-L1 adipocytes treated with the methanol extract of *Garcinia mangostana* (AR 933) as indicated. Protein expressions were densitometrically analyzed and normalized with the actin expression. Bar diagram in each panel shows normalized protein expressions in arbitrary units. In bar diagrams, the bars represent protein expression in cells treated with vehicle control (a), 2.5 µg/ml (b) and 5.0 µg/ml (c) of AR 933, respectively.

Further, random screening studies have shown surprisingly that the methanol extract of Garcinia mangostana (AR 933) rind possesses potent α-amylase and α-glucosidase inhibitory activities in enzymatic studies and exhibited potent anti-adipogenesis activity in cell based in vitro assays in 3T3-L1 cells. The most active compounds were found to be α-mangostin (2) and γ-mangostin (3) during the bio-assay guided separation of the methanol extract. The methanol extract comprising α-mangostin and/or γ-mangostin also showed potent pro-lipolytic and anti-adipogenesis activity. The methanol extract also significantly ameliorated the levels of various key biomarker molecules or biological proteins those are primarily responsible for the adipogenesis and lipid break down processes, insulin resistance in type 2 diabetes, in metabolic disorders and disease conditions associated with metabolic syndrome. These include PPARγ, ADRP, adipocyte CD36, aP2/FABP4/A-FABP, β3AR, adiponectin, Perilipin and PTP-1B (FIGS. 5, 8 and 9). It is also interesting to note that AR 933 also potently inhibited the macrophage CD36, MCP-1, and oxidized LDL in high glucose induced macrophage cells (FIG. 8). Altogether, These suggest that AR 933 can also be used as a potential candidate to treat obesity, cardiovascular manifestations such as atherosclerosis, metabolic syndrome and other metabolic disorders.

The inventors have then randomly prepared and tested several compositions comprising the extracts of Sphaeranthus indicus in combination with several plant extracts in an effort to find a composition that can show better efficacy in ameliorating the metabolic processes and in the expression or production of biomarker molecules associated with metabolic disorders, and to identify a better agent for controlling, treating and preventing obesity, metabolic syndrome and disease conditions associated with metabolic syndrome and metabolic disorders. It was found accidentally that compositions comprising at least one phytochemical component selected from the extract(s) or fractions or enriched fraction(s) or compound(s) derived from Sphaeranthus indicus in combination with at least one phytochemical component selected from extracts or enriched fractions or compounds derived from Garcinia mangostana can be very effective in the amelioration of certain metabolic processes and modulation of some important metabolic biomarkers involved in the metabolic processes.

The metabolic processes controlled by the above compositions include anti-adipogenesis and pro-lipolysis, and α-amylase and α-glucosidase enzyme inhibitions. The biomarkers ameliorated by the above compositions include but not limited to MMP-1, MMP-3, PPARγ, ADRP, adipocyte CD36, macrophage CD36, MCP-1, Ox-LDL, aP2/FABP4/A-FABP, β3AR, adiponectin, Perilipin and PTP-1B.

Figure 6:
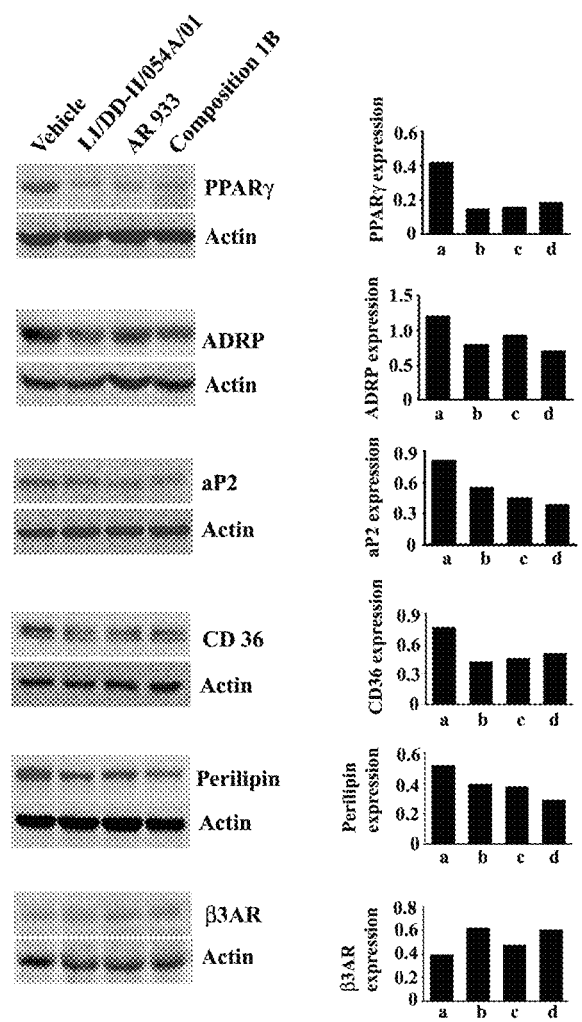
FIG. 6: Representative immuno blots show the modulations of PPAR (A), ADRP (B), aP2 (C), CD36 (D), perilipin (E) and β3AR (F) protein expressions in 3T3-L1 adipocytes treated with either *Sphaeranthus indicus* ethyl acetate extract (LI/DD-II/054A/01) or *Garcinia mangostana* methanol extract (AR 933) or composition 1B comprising these two extracts as indicated. Protein expressions were densitometrically analyzed and normalized with the actin expression. Bar diagram in each panel shows normalized protein expressions in arbitrary units. In bar diagrams, the bars represent protein expressions in cells treated with vehicle control (a), LI/DD-II/054A/01 (b), AR 933 (c) and composition 1B (d).

More importantly, it was further observed accidentally that there was a synergistic inhibitory effect between the extracts of these two herbs in the amelioration of certain metabolic processes and modulation of some important metabolic biomarkers involved in the metabolic processes when they are combined rather than using the individual constituents separately. The composition 1B, for example, obtained by combining unit doses of ethyl acetate extract (LI/DD-II/054A/01) and Garcinia mangostana methanol extract (AR 933) in 1:3 ratio showed synergistic inhibition of selected biomarker proteins such as ADRP, aP2, perilipin and PTP-1B in adipocyte 3T3-L1 cells and CD36, MCP-1 and Ox-LDL in mouse macrophage cells as shown in FIGS. 6, 7 and 9. In addition, composition 1B also showed synergistic enhancement of the production of adiponectin in adipocyte cells (FIG. 8). The efficacy shown by the composition is better than the effects exhibited by each of the individual ingredients.

Figure 13:
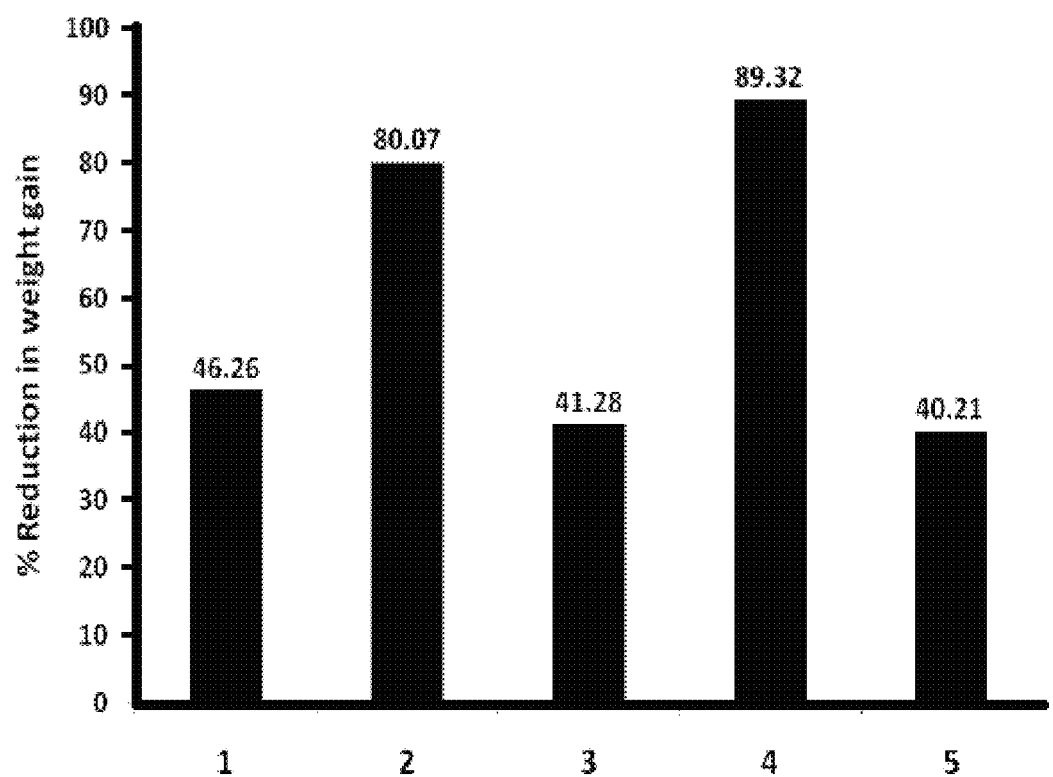
FIG. 13: Bar diagram representation of % reduction in body weight in diet induced obese model of Sprague Dawley rats. The bars 1 to 5 represent % reductions in body weight in treatment groups supplemented with LI/DD-II/054A/03 (100 mg/kg), LI/DD-II/054A/03 (250 mg/kg), AR 933 (250 mg/kg), composition 1D (250 mg/kg) and sibutramine (7 mg/kg) respectively.

The potent anti-obesity properties and synergistic effects shown by the extracts of Sphaeranthus indicus and Garcinia mangostana and their compositions in in vitro models were further evaluated in an in vivo model of obesity. Obesity was induced in male Sprague Daley rats by supplementing the rats with High Fat diet for eight weeks. After eight weeks of induction period, the rats were randomly allocated to various groups with seven animals in each group and the animals belonged to the treatment groups were orally supplemented daily with 100 or 250 mg/kg body weight of methanol extract of Sphaeranthus indicus (LI/DD-II/054A/03) or 250 mg/kg body weight of AR 933 or 250 mg/kg body weight of composition 1D containing LI/DD-II/054A/03 and AR 933 in 3:1 ratio, each in 10 mL of 0.5% CMC in water for further 8 weeks. The control group of animals received only the vehicle (10 mL of 0.5% CMC in water). Body weight of individual animal was recorded weekly, and mean body weight of the animals in each group was determined. The body weight gain was calculated at the end of 1st week, 4th week and 8th week after initiation of treatment in comparison to respective initial body weight. LI/DD-II/054A/03 dose dependently inhibited the body weight gain in treatment group of rats. The rats supplemented with 100 mg/kg body weight of LI/DD-II/054A/03 exhibited 46.3% reduction in body weight gain in comparison with the control animals. Similarly, AR 933 and LI/DD-II/054A/03 at a daily dose of 250 mg/kg exhibited 41.3% and 80.1% reductions in body weight gain respectively. Interestingly, the composition 1D at the same dose level (250 mg/kg) exhibited more potent and significant reduction in body weight gain (89%) compared to the vehicle treated control group. The results of body weight gain for the treatment groups and control group are summarized in FIG. 13.

From the foregoing, it is obvious that the reduction in weight gain shown by the composition 1D comprising Sphaeranthus indicus methanol extract (LI/DD-II/054A/03) and methanol extract of Garcinia mangostana (AR 933) in 3:1 ratio is better than the effect shown by the individual ingredients LI/DD-II/054A/03 and AR 933, manifesting a synergistic effect between these two ingredients.

Even though a few selected extracts have been used in this study, this invention covers all extracts, active fractions and active compounds of the Sphaeranthus indicus, which comprises the active ingredient 7-hydroxyfrullanolide or other active ingredient(s) in the range of 0.1% to 99.9%. Preferably any organic solvent extract of Sphaeranthus indicus or a fraction or pure compound derived from the extract with or without standardization to 7-hydroxyfrullanolide can be used. The medium for obtaining active extract may be selected from either organic solvents or water or mixtures of organic solvent and water, preferably an organic solvent. The list of organic solvents include but not limited to hexane, dichloromethane, chloroform, ethyl acetate, acetone, methanol, ethanol, n-butanol, iso-propanol, methyl isobutyl ketone etc or the mixtures thereof. The crude extracts may be used as they are as a medicament or for making the compositions. Alternatively, the extracts may be enriched to any designated concentration of 7-hydroxyfrullanolide or one or more active ingredients in the range of 0.1% to 99.9% using solvent partitions or washings or column chromatography on silica or reversed phase silica or resin column using organic or aqueous solvents or mixtures thereof or crystallizations or combinations thereof prior to using them directly for desired health application of the invention or for making the compositions.

Similarly, methanol extract of *Garcinia mangostana* has been used to demostrate the present invention. However, any organic solvent extract extract or mixed organic solvent extract or water or an extract obtained by an extraction with a mixed solvent comprising water and water miscible organic solvent and can also be used.

The present novel and inventory compositions comprise different aspects of the invention cited below:

The word "component" widely used in the specification and claims of the present invention refers to herb powders, extracts, fractions, enriched fractions, active compounds or phytochemicals and phytochemical actives. The word "component" is used in the description from now onwards as a substitute to these terms.

The extract(s), fraction(s), active compound(s), phytochemicals or mixtures thereof derived from *Sphaeranthus indicus* can be used as pharmaceutical/dietary supplement/food ingredients for the prevention, treatment and control of obesity, diabetes, atherosclerosis, metabolic syndrome and other metabolic disorders.

The pharmaceutical/dietary supplement/food ingredients mentioned in the present invention refers to the extract(s), fraction(s), active compound(s), phytochemicals or mixtures thereof derived from *Sphaeranthus indicus*.

In an important aspect, the invention provides pharmaceutical/dietary supplement/food ingredient composition(s) comprising at least one component selected from the extract(s), fraction(s), active compound(s) and phytochemical(s) or mixtures thereof derived from *Sphaeranthus indicus* and at least one component selected from the extract(s), fraction(s), active compound(s) and phytochemicals or mixtures thereof derived from *Garcinia mangostana*, optionally comprising one or more selected from biologically active components derived from plants, animals and microorganisms, pharmaceutically or dietetically acceptable active ingredients, vitamins, minerals, vehicles, carriers and diluents or mixtures thereof.

In the other important aspect the invention provides, pharmaceutical/dietary supplement/food ingredient(s) comprising at least one component selected from the extract(s) or fraction(s) or active compound(s) or phytochemicals or mixtures thereof derived from *Sphaeranthus indicus* for the control, prevention and treatment of one or more disease conditions selected from but not limited to obesity, weight loss, diabetes, atherosclerosis, arteriosclerosis, cardiovascular diseases, neurological disorders, Alzheimer's, cognitive disorders, oxidative stress, skin disorders, aging of the skin, UV irradiated damage, hypertension, hypercholesteremia (LDL, HDL, VLDL), hyperlipidemia (triglycerides), immune deficiency, cancer, metabolic syndrome and other metabolic disorders.

In another aspect the invention provides the pharmaceutical/dietary supplement/food ingredient compositions comprising at least one component selected from the extract(s), fraction(s), active compound(s), phytochemical(s) or mixtures thereof derived from *Sphaeranthus indicus* in combination with one or more selected from biologically active components derived from plants, animals and microorganisms, pharmaceutically or dietetically acceptable active ingredients, vitamins, minerals, vehicles, carriers and diluents or mixtures thereof for the control, prevention and treatment of one or more disease conditions selected from but not limited to obesity, weight loss, diabetes, atherosclerosis, arteriosclerosis, cardiovascular diseases, neurological disorders, Alzheimer's, cognitive disorders, oxidative stress, skin disorders, aging of the skin, UV irradiated damage, hypertension, hypercholesteremia (LDL, HDL, VLDL), hyperlipidemia (triglycerides), immune deficiency, cancer, metabolic syndrome and other metabolic disorders.

In another aspect, the invention provides the pharmaceutical/dietary supplement/food ingredient compositions comprising at least one component selected from the extract(s), fraction(s) and active compound(s), phytochemical(s) or mixtures thereof derived from *Sphaeranthus indicus* and at least one component selected from the extract(s), fraction(s) and active compound(s), phytochemical(s) or mixtures thereof derived from *Garcinia mangostana*, optionally containing one or more selected from biologically active components derived from plants, animals and microorganisms, pharmaceutically or dietetically acceptable active ingredients, vitamins, minerals, vehicles, carriers and diluents or mixtures thereof for the control and prevention and treatment of one or more disease conditions selected from but not limited to obesity, weight loss, diabetes, atherosclerosis, arteriosclerosis, cardiovascular diseases, neurological disorders, Alzheimer's, cognitive disorders, oxidative stress, skin disorders, aging of the skin, UV irradiated damage, hypertension, hypercholesteremia (LDL, HDL, VLDL), hyperlipidemia (triglycerides), immune deficiency, cancer, metabolic syndrome and other metabolic disorders.

In another aspect the invention provides the pharmaceutical/dietary supplement/food ingredient compositions comprising at least one component selected from the extract(s), fraction(s), active compound(s) or phytochemical(s) or mixtures thereof derived from *Sphaeranthus indicus* and at least one component selected from the extract(s), fraction(s), active compound(s) or phytochemical(s) or mixtures thereof derived from *Garcinia mangostana*, optionally containing one or more selected from biologically active components derived from plants, animals and microorganisms, pharmaceutically or dietetically acceptable active ingredients, vitamins, minerals, vehicles, carriers and diluents or mixtures thereof for the amelioration of the expression or production of at least one biomarker protein selected from but not limited to Matrix Metalloproteinase-1 (MMP-1), Matrix Metalloproteinase-3 (MMP-3), C-reactive protein (CRP), PPAR-γ, Adipose Differentiation Related Protein (ADRP), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin and Protein tyrosine phosphatase 1B (PTP 1B).

In another aspect, the invention provides the pharmaceutical/dietary supplement/food ingredient(s) comprising at least one component selected from the extract(s) or fraction(s) or active compound(s) or phytochemical(s) or mixtures thereof derived from *Sphaeranthus indicus*, and the compositions comprising at least one said component derived from *Sphaeranthus indicus* in combination with one or more selected from biologically active components derived from plants, animals and microorganisms, pharmaceutically or dietetically acceptable active ingredients, vitamins, minerals, vehicles, carriers and diluents or mixtures thereof for the amelioration of the expression or production of at least one biomarker protein related to or associated with metabolic syndrome, obesity and other metabolic disorders selected from but not limited to Matrix Metalloproteinase-1 (MMP-1), Matrix Metalloproteinase-3 (MMP-3), C-reactive protein (CRP), PPAR-γ, Adipose Differentiation Related Protein (ADRP), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin and Protein tyrosine phosphatase 1B (PTP 1B).

In another aspect, the invention provides, the pharmaceutical/dietary supplement/food ingredient(s) comprising at least one component selected from the extract(s) or fraction(s) or active compound(s) or phytochemical(s) or mixtures thereof derived from *Sphaeranthus indicus*, and their compositions in combination with one or more selected from biologically active components derived from plants, animals and microorganisms, pharmaceutically or dietetically acceptable active ingredients, vitamins, minerals, vehicles, carriers and diluents or mixtures thereof for controlling one or more of the metabolic processes selected from acceleration of lipolysis, inhibition of adipogenesis, inhibition of alpha-amylase and inhibition of alpha-glucosidase.

In another aspect, the invention provides pharmaceutical/dietary supplement/food ingredient composition comprising at least one component selected from the extract(s), fraction(s), active compound(s) and phytochemical(s) or mixtures thereof derived from *Sphaeranthus indicus* in combination with at least one component selected from the extract(s), fraction(s), active compound(s) and phytochemical(s) or mixtures thereof derived from *Garcinia mangostana*.

In another aspect, the invention provides pharmaceutical/dietary supplement/food ingredient compositions comprising at least one component selected from the extract(s), fraction(s), active compound(s) and phytochemical(s) or mixtures thereof derived from *Sphaeranthus indicus* and at least one component selected from the extract(s), fraction(s), active compound(s) and phytochemical(s) or mixtures thereof derived from *Garcinia mangostana*, optionally containing one or more selected from biologically active components derived from plants, animals and microorganisms, pharmaceutically or dietetically acceptable active ingredients, vitamins, minerals, vehicles, carriers and diluents or mixtures thereof, wherein the percentage of *Sphaeranthus indicus* derived component in the composition varies in the range from 0.01% to 99.9% and the percentage of *Garcinia mangostana* derived component varies in the range from 99.9% to 0.01%.

In another aspect the invention provides the pharmaceutical/dietary supplement/food ingredient compositions comprising at least one component selected from the extract(s), fraction(s), active compound(s), phytochemicals or mixtures thereof derived from *Sphaeranthus indicus* in combination with one or more selected from biologically active components derived from plants, animals and microorganisms, pharmaceutically or dietetically acceptable active ingredients, vitamins, minerals, vehicles, carriers and diluents or mixtures thereof, wherein the percentage of *Sphaeranthus indicus* derived component in the composition varies in the range from 0.01% to 99.9%.

In another aspect, the pharmaceutical/dietary supplement/food ingredient compositions comprising at least one component selected from the extract(s), fraction(s), active compound(s) and phytochemical(s) or mixtures thereof derived from *Sphaeranthus indicus* and at least one component selected from the extract(s), fraction(s), active compound(s) and phytochemical(s) or mixtures thereof derived from Garcinia *mangostana*, optionally containing one or more selected from biologically active components derived from plants, animals and microorganisms, pharmaceutically or dietetically acceptable active ingredients, vitamins, minerals, vehicles, carriers and diluents or mixtures thereof, comprise at least one *Sphaeranthus indicus* derived frullanolide/eudesmanoid sesquiterpene compound selected from but not limited to frullanolides, 7-hydroxyfrullanolide; 11α,13-dihydro-3α,7α-dihydroxy-4,5-epoxy-6β,7-eudesmanolide; 11α,13-dihydro-7α-acetoxy-3β-hydroxy-6β,7-eudesm-4-enolide; 3-keto-β-eudesmol; 11α,13-dihydro-3α,7α-dihydroxyeudesm-4-en-6α,12-olide; 11α,13-dihydro-3α,7α-dihydroxyfrullanolide; 11α,13-dihydro-7α,13-dihydroxyfrullanolide; 11α,13-dihydro-7α-hydroxy-13-methaoxyfrullanolide; 2α,7α-dihydroxy-4-en-11,13-dihydroeudesm-6,12-olide; 2α-hydroxycostic acid; 3-keto-7α-hydroxyeudesm-4-en-6,12-olide (cryptomeridiol); 4-epicryptomeridiol; sphaeranthanolide; 2α-hydroxysphaerantholide; 2α-acetoxysphaerantholide; 2α,7α-dihydroxysphaerantholide; 2α-acetoxy-7α-hydroxysphaerantholide; 2α-acetoxy-5α-hydroxyisosphaerantholide or mixtures thereof, preferably 7-α-hydroxy-4,11(13)-eudesmadien-12,6-olide also known as 7-hydroxyfrullanolide or related compounds or its analogs derived from *Sphaeranthus indicus*.

In another aspect, pharmaceutical/dietary supplement/food ingredient(s) comprising at least one component selected from extract(s), fraction(s), active compound(s) and phytochemical(s) or mixtures thereof derived from *Sphaeranthus indicus* and their compositions comprising at least one said phytochemical component derived from *Sphaeranthus indicus* in combination with one or more selected from biologically active components derived from plants, animals and microorganisms, pharmaceutically or dietetically acceptable active ingredients, vitamins, minerals, vehicles, carriers and diluents or mixtures thereof, comprise at least one *Sphaeranthus indicus* derived frullanolide/eudesmanoid sesquiterpene compound selected from but not limited to frullanolides, 7-hydroxyfrullanolide; 11α,13-dihydro-3α,7α-dihydroxy-4,5-epoxy-6β,7-eudesmanolide; 11α,13-dihydro-7α-acetoxy-3β-hydroxy-6β,7-eudesm-4-enolide; 3-keto-β-eudesmol; 11α,13-dihydro-3α,7α-dihydroxyeudesm-4-en-6α,12-olide; 11α,13-dihydro-3α,7α-dihydroxyfrullanolide; 11α,13-dihydro-7α,13-dihydroxyfrullanolide; 11α,13-dihydro-7α-hydroxy-13-methaoxyfrullanolide; 2α,7α-dihydroxy-4-en-11,13-dihydroeudesm-6,12-olide; 2α-hydroxycostic acid; 3-keto-7α-hydroxyeudesm-4-en-6,12-olide (cryptomeridiol); 4-epicryptomeridiol; sphaeranthanolide; 2α-hydroxysphaerantholide; 2α-acetoxysphaerantholide; 2α,7α-dihydroxysphaerantholide; 2α-acetoxy-7α-hydroxysphaerantholide; 2α-acetoxy-5α-hydroxyisosphaerantholide or mixtures thereof, preferably 7-α-hydroxy-4,11(13)-eudesmadien-12,6-olide also known as 7-hydroxyfrullanolide or related compounds or its analogs derived from *Sphaeranthus indicus*.

In another aspect, the invention provides the component(s) selected from the extract(s) or fraction(s) or active compound(s) or phytochemical(s) or mixtures thereof derived from *Sphaeranthus indicus*, and their compositions as described above, wherein the active compounds in *Sphaeranthus indicus* derived component responsible for the prevention, treatment and control of obesity, metabolic syndrome and other metabolic disorders include, but not limited to, frullanolide/eudesmanoid sesquiterpenes, preferably 7-α-Hydroxy-4, 11 (13)-eudesmadien-12,6-olide also known as 7-hydroxyfrullanolide.

The 7-hydroxyfrullanolide or the related compounds used for the prevention, treatment and control of obesity, metabolic syndrome and other metabolic disorders or for making the composition of the present invention can be naturally derived or can be produced through synthesis or semisynthesis.

In another aspect, the invention provides the *Sphaeranthus indicus* derived component selected from the extracts, fractions, active compounds and phytochemicals, or mixtures thereof used for the prevention, treatment and control of obesity, metabolic syndrome and other metabolic disorders or for making the compositions described above comprises, wherein the concentration of active compound 7-hydroxyfrullanolide/other frullanolide/eudesmanoid sesquiterpene(s)/other phytochemicals in the extract(s) and fraction(s) derived from *Sphaeranthus indicus* varies in the range of 0.001% to 100%, preferably 0.01 to 99%.

In another aspect, the concentration of the concentration of active compound 7-hydroxyfrullanolide/other frullanolide/eudesmanoid sesquiterp ene(s)/other phytochemicals in the compositions comprising *Sphaeranthus indicus* derived component as described in the previous embodiments varies in the range from 0.001% to 99%, preferably 0.01 to 95% by weight.

In another aspect, the invention provides the compositions comprising components derived from *Garcinia* species and preferably *Garcinia mangostana* for the control, prevention and treatment of obesity, metabolic syndrome and other metabolic disorders, wherein the active compounds include but not limited to xanthones preferably α-mangostin and γ-mangostin.

In another aspect, the invention provides the compositions comprising at least one component selected from the extracts, fractions, enriched fractions, compounds derived from *Garcinia mangostana* as described in the previous embodiments, wherein the concentration of active compounds, α-mangostin and γ-mangostin, either individually or jointly in *Garcinia mangostana* derived extract(s) or fraction(s) varies from 0.001% to 99.9%.

In another aspect, the invention provides the compositions comprising at least one component selected from the extracts, fractions, enriched fractions, compounds derived from *Garcinia mangostana* as described in the previous embodiments, wherein the concentration of active compounds α-mangostin and γ-mangostin in the compositions varies either individually or together from 0.001% to 99%, preferably 0.01 to 95%

In another aspect, the invention provides the pharmaceutical/dietary supplement/food ingredient compositions comprising at least one component selected from the extract(s), fraction(s), active compound(s) and phytochemical(s) or mixtures thereof derived from *Sphaeranthus indicus* and at least one component selected from the extract(s), fraction(s), active compound(s) and phytochemical(s) or mixtures thereof derived from *Garcinia mangostana*, for the amelioration of the expression or production of at least one metabolic biomarker molecule selected from but not limited to Matrix Metalloproteinase-1 (MMP-1), Matrix Metalloproteinase-3 (MMP-3), C-reactive protein (CRP), PPAR-γ, Adipose Differentiation Related Protein (ADRP), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin and Protein tyrosine phosphatase 1B (PTP 1B).

In another aspect, the invention provides pharmaceutical/dietary supplement/food ingredient(s) selected from the extract(s), fraction(s), active compound(s) and phytochemicals or mixtures thereof derived from *Sphaeranthus indicus* or their compositions, wherein the amelioration of metabolic processes responsible for obtaining claimed health benefits can be selected from but not limited to lipolysis and adipogenesis, fat breakdown, fat cell regeneration or by any other mechanism associated with or related to thereof.

In other embodiment, the invention provides frullanolide/eudesmanolide and related compounds, preferably 7-hydroxyfrullanolide or its analogs or the compositions comprising the said compounds in combination with at least one component selected from biologically active components derived from plants, animals and microorganisms, pharmaceutically or dietetically acceptable active ingredients, vitamins, minerals, vehicles, carriers and diluents or mixtures thereof for the control, prevention and treatment of one or more disease conditions selected from but not limited to obesity, weight loss, diabetes, atherosclerosis, metabolic syndrome and other metabolic disorders.

In other embodiment, the invention provides, frullanolide/eudesmanolide and related compounds, preferably 7-hydroxyfrullanolide or its analogs or the compositions comprising the said compounds as described abobe for the amelioration of the expression or production of at least one metabolic biomarker molecules including but not limited to Matrix Metalloproteinase-1 (MMP-1), Matrix Metalloproteinase-3 (MMP-3), C-reactive protein (CRP), PPAR-γ, Adipose Differentiation Related Protein (ADRP), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin and Protein tyrosine phosphatase 1B (PTP 1B)

In another aspect, the invention provides compositions comprising Garcinia *mangostana* derived component, wherein said extract(s), fraction(s), active compound(s) and phytochemicals or mixtures thereof derived from Garcinia *mangostana* exhibit inhibitory effects against carbohydrate absorption inhibition enzymes including but not limited to alpha-amylase and alpha-glucosidase and for the inhibition of adipogenesis.

In another aspect of the invention, the biologically active components used for making the compositions described in the previous embodiments can be selected from the extracts or fractions or pure compounds or phytochemical(s) or powders derived from plants, animals and microorganisms having any health benefit selected from but not limited to anti-diabetic activity, anti-hyperglycemic activity, hypolipidemic activity, anti-obesity activity, anti-hypertensive activity, anti-platelet aggregation activity, anti-infective activity, anti-atherosclerotic activity and anti-inflammatory activity, anti-oxidant(s) and bio-enhancing activity.

In another aspect, the invention provides pharmaceutical/dietary supplement/food ingredients derived from *Sphaeranthus indicus* described in preceding embodiments, wherein said extract(s) or active fraction(s) or active compound(s) or phytochemicals or mixtures thereof are derived from at least one of the plant parts selected from but not limited to leaves, flower heads, stem, bark, root, whole plant or mixtures thereof, preferably flower heads.

In another aspect of the invention, pharmaceutical/dietary supplement/food ingredients and their compositions as described in previous embodiments, wherein said extract(s) or active fraction(s) or active compound(s) or phytochemicals or mixtures thereof derived from *Sphaeranthus indicus* and *Garcinia mangostana* are obtained through extraction using solvents selected from one or more of organic solvents, alcohols, hydroalcohols, water or mixtures thereof.

In another aspect of the invention, the extract(s) or active fraction(s) or active compound(s) or phytochemicals or mixtures thereof derived from *Garcinia mangostana* are derived from the whole fruit or fruit rind or fruit pulp of *Garcinia* and preferably Garcinia *mangostana*.

In another embodiment, the extract(s), fraction(s), active compound(s) and phytochemical(s) or mixtures thereof can be derived from any *Sphaeranthus* species selected from but not limited to *Sphaeranthus indicus, Sphaeranthus amaranthoides, S. africanus, S. volgensis, S. kotchyi, S. suaveolens* can also used for intended health application or for preparing components or compositions claimed in the present invention.

In another embodiment extract(s), fraction(s), active compound(s) and phytochemical(s) or mixtures thereof used for making the composition can be derived from other *Garcinia* species including but not limited to *Garcinia* cambogia, G. hanburyii, G. schomburgkiana, G. dulcis, G. thorelii, G. xanthochymus, G. cowa, G. bracteata, G. pyrifera and G. nervosa.

The examples of the biologically or pharmaceutically acceptable carriers employed in the present invention include, but are not limited to, surfactants, excipients, binders, diluents, disintegrators, lubricants, preservatives, stabilizers, buffers, suspensions and drug delivery systems.

In another aspect, the invention provides pharmaceutical/dietary supplement/food ingredient compositions, as described in previous embodiments, comprising at least one component extract(s) or fraction(s) or active compound(s) or phytochemical(s) or mixtures thereof derived from *Sphaeranthus indicus* in combination with at least one component selected from the excipients, carriers and diluents, wherein preferred examples of solid carriers or diluents or excipients include but not limited to glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives and preferred examples of liquid carriers or diluents or excipients include but not limited to distilled water, saline, aqueous glucose solution, alcohol (e.g. ethanol), propylene glycol and polyethylene glycol; and oily carriers such as various animal and vegetable oils, white soft paraffin, paraffin and wax.

In another aspect, the invention provides pharmaceutical/dietary supplement/food ingredient(s) or their composition(s) as claimed in preceding embodiments, wherein said component or composition is administered orally, topically or parenterally or by inhalation to a subject or mammal or warm blooded animal in need thereof.

In another aspect, the invention provides pharmaceutical/dietary supplement/food ingredient(s) or their composition(s) as claimed in preceding embodiments, wherein said components or compositions can be formulated as oral agents such as tablets, soft capsule, hard capsule, pills, granules, powders, emulsions, suspensions, syrups, pellets, food, beverages and the like; and parenteral agents such as injection solution, drops, suppositories and the like; and transdermal agents such as patches, topical creams and gel, and food ingredients or beverages.

In another aspect, the invention provides a method for the control/prevention/treating of a disease condition selected from but not limited to obesity, Metabolic Syndrome and other metabolic disorders comprising administering to a subject in need thereof a therapeutically effective amount of at least one pharmaceutical/dietary supplement/food ingredient selected from the extract(s), fraction(s), active compound(s), phytochemical(s) or mixtures thereof derived from *Sphaeranthus indicus* or their composition(s) as described in preceeding embodiments.

In another aspect, the invention provides provides a method of promoting lipolysis and/or inhibiting adipogenesis comprising administering to a subject or mammal or warm blooded animal in need thereof a therapeutically effective quantity of at least one pharmaceutical/dietary supplement/food ingredient(s) derived from *Sphaeranthus indicus* or their composition(s) as described in preceeding embodiments.

A method of inhibiting adipogenesis or inhibiting digestive enzymes selected from but not limited to alpha-amylase and/or alpha-glucosidase comprising administering to a subject or mammal or warm blooded animal in need thereof a therapeutically effective quantity of at least one component selected from the extract(s), fraction(s), active compound(s), phytochemical(s) or mixtures thereof derived from *Garcinia mangostana* or the compositions comprising the said *G. mangostana* derived component(s).

In another aspect, the invention provides a method of treating obesity, diabetes, metabolic syndrome or other metabolic disorders comprising administering to a subject or animal in need thereof a therapeutically effective amount of at least one component selected from extract(s) or fraction(s) or active compound(s) or phytochemical(s) or mixtures thereof derived from *Sphaeranthus indicus* or their compositions, preferably in combination with at least one component selected from the extract(s), fraction(s) and active compound(s) or mixtures thereof derived from *Garcinia mangostana*, optionally containing one or more of biologically active components derived from plants, animals and microorganisms, pharmaceutically or dietetically acceptable active ingredients, vitamins, minerals, vehicles, carriers and diluents or mixtures thereof.

In another aspect, the invention provides a method of using components selected from the extract(s) or fraction(s) or active compound(s) or phytochemical(s) or mixtures thereof derived from *Sphaeranthus indicus* and their compositions for the amelioration the expression or production of biological markers selected from but not limited to Matrix Metalloproteinase-1 (MMP-1), Matrix Metalloproteinase-3 (MMP-3), C-reactive protein (CRP), PPAR-γ, Adipose Differentiation Related Protein (ADRP), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin and Protein tyrosine phosphatase 1B (PTP 1B).

In another aspect, the invention provides a method of amelioration the expression of biological markers selected from but not limited to Matrix Metalloproteinase-1 (MMP-1), Matrix Metalloproteinase-3 (MMP-3), PPAR-γ, Adipose Differentiation Related Protein (ADRP), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin and Protein tyrosine phosphatase 1B (PTP 1B) comprising administering to a subject or an animal in need thereof a therapeutically effective amount of at least one component selected from the extract(s) or fraction(s) or active compound(s) or phytochemical(s) or mixtures thereof derived from *Sphaeranthus indicus* and their compositions as described in the preceeding embodiments.

In another aspect, the invention provides phytochemical components such as extract(s) or fraction(s) or active compound(s) or phytochemical(s) or mixtures thereof derived from *Sphaeranthus indicus* or the compositions comprising the said *Sphaeranthus indicus* derived components for ameliorating one or more metabolic processes selected from promoting lipolysis, inhibiting adipogenic activity, fat breakdown, fat cell regeneration or by any other mechanism associated with or related to thereof.

In another aspect, the invention provides components such as extract(s) or active fraction(s) or active compound(s) or phytochemical(s) or mixtures thereof derived from Garcinia *mangostana* and their compositions for inhibiting carbohydrate break-down enzymes such as alpha-amylase and/or alpha-glucosidase.

In another aspect, the invention provides components such as extract(s) or fraction(s) or active compound(s) or phytochemical(s) or mixtures thereof derived from Garcinia *mangostana* for treating obesity and metabolic syndrome through anti-adipogenic activity.

In another aspect, the invention provides compositions comprising at least components selected from the extract(s) or fraction(s) or active compound(s) or phytochemical(s) or mixtures thereof derived from *Sphaeranthus indicus* and at least one component selected from the extract(s) or active fraction(s) or active compound(s) or phytochemical(s) or mixtures thereof derived from *Garcinia mangostana*, for digestive enzyme inhibition/carbohydrate absorption inhibition such as alpha-amylase inhibition, alpha-glucosidase inhibition for the prevention and treatment of obesity, diabetes, metabolic syndrome or disease conditions associated with metabolic syndrome.

In another aspect, the invention provides the pharmaceutical/dietary supplement/food ingredient(s) selected from the extract(s), fraction(s), active compound(s) or phytochemical(s) or mixtures thereof derived from *Sphaeranthus indicus* and their compositions in combination with at least one component selected from the extract(s), fraction(s), active compound(s) or phytochemical(s) or mixtures thereof derived from Garcinia *mangostana* as described in preceeding embodiments for anti-adipogenic activity, promoting lipolysis, fat breakdown, fat cell regeneration or by any other mechanism associated with or related to thereof.

In a further embodiment of the present invention, the components selected from extract(s), fraction(s), active compound(s) or phytochemical(s) or mixtures thereof derived from *Sphaeranthus indicus* or their compositions as described above can be optionally combined with bioavailability enhancing agents selected from but not limited to extract(s), fraction(s), pure compound(s) derived from *Piper nigrum* extract(s) and *Piper longum*, piperine.

In alternative aspect of the invention, the components selected from extract(s), fraction(s), active compound(s) or phytochemical(s) or mixtures thereof derived from *Sphaeranthus indicus* or their compositions claimed in the present invention are delivered in the form of controlled release tablets, using controlled release polymer-based coatings by the techniques including nanotechnology, microencapsulation, colloidal carrier systems and other drug delivery systems known in the art. The said formulation can be designed for once a daily administration or multiple administrations per day.

In other aspect of the invention, the components selected from extract(s), fraction(s), active compound(s) or phytochemical(s) or mixtures thereof derived from *Sphaeranthus indicus* or their compositions claimed in the present invention can also be formulated into or added to existing or new food and beverage form(s) and animal feeds as a healthy food or beverage or feed for control, prevention and treatment of several diseases including but not limited to obesity, weight loss, diabetes, atherosclerosis, arteriosclerosis, cardiovascular diseases, neurological disorders, Alzheimer's, cognitive disorders, oxidative stress, skin disorders, aging of the skin, UV irradiated damage, hypertension, hypercholesteremia (LDL, HDL, VLDL), hyperlipidemia (triglycerides), immune deficiency, cancer, metabolic syndrome and other metabolic disorders.

The unexpected and superior ameliorating effects of the extract(s), fraction(s) and active compound(s) or phytochemical(s) or mixtures thereof derived from *Sphaeranthus indicus* and their compositions in combination with extract(s), fraction(s), active compound(s) or phytochemical(s) or mixtures thereof derived from Garcinia *mangostana* on the enzymes, metabolic biological markers and metabolic processes related to one or more of obesity, metabolic syndrome and other metabolic disorders are illustrated by the following non-limiting examples:

Example 1

*Sphaeranthus indicus* Ethyl Acetate Extract (LI/DD-II/054A/01)

*Sphaeranthus indicus* flower heads (2.2 kg) were charged into a pilot extractor and extracted with ethyl acetate (22 L) at reflux temperature for 2 h. The extract was filtered and the spent raw material was re-extracted twice with ethyl acetate (2×13 L) under similar conditions. The combined extract was fine filtered and concentrated over a climbing film evaporator to obtain residue (174 g). The ethyl acetate extract showed 11% of 7-hydroxy-4, 11 (13)-eudesmadien-12,6-olide (7-hydroxyfrullanolide) by HPLC method of analysis.

Example 2

*Sphaeranthus indicus* Hexane Extract (LI/DD-II/054A/02):

*Sphaeranthus indicus* flower heads (1.0 kg) were taken in a Soxhlet apparatus and extracted with hexane (6 L) at reflux temperature for 4 h. The extract was fine filtered and the spent raw material was re-extracted twice with hexane (2×4 L). The extracts were combined and concentrated under vacuum to obtain a residue (43 g). The hexane extract showed 21% of 7-hydroxyfrullanolide by HPLC method of analysis.

Example 3

*Sphaeranthus indicus* Methanol Extract (LI/DD-II/054A/03):

*Sphaeranthus indicus* flower heads (1 kg) were taken in a RB flask and extracted with methanol (8 L) at 80° C. temperature for 2 h. The extract was filtered and the spent raw material was re-extracted twice with ethyl acetate (2×6 L) under similar conditions. The combined extract was fine filtered and concentrated over a climbing film evaporator to obtain a residue (110 g). The methanol extract (LI/DD-II/054A/03) showed 8.3% of 7-hydroxyfrullanolide by HPLC method of analysis.

Example 4

Purification of 7-Hydroxyfrullanolide (LI054A01):

The ethyl acetate extract (90 g) of the flower heads of *Sphaeranthus indicus* was subjected to chromatography over a silica column using eluants of increasing polarity from hexane to acetone. The fractions eluted with 20% acetone/hexane were combined and evaporated under vacuum to give a residue (16 g) containing 63% of 7-hydroxyfrullanolide. The residue was subjected to re-chromatography over silica using solvents of increasing polarity from hexane to ethyl acetate. The fractions eluted with 20-25% ethyl acetate/hexane yielded were combined and evaporated and the residue was precipitated from acetonitrile to obtain semi-pure 7-hydroxyfrullanolide (91%). The residue was finally purified on silica column using chloroform/hexane mixtures. The fractions eluted with 25-35% chloroform/hexane were combined and evaporated to give pure 7-hydroxyfrullanolide (7.3 g, 99%).

Example 5

*Garcinia mangostana* Methanol Extract (AR 933):

Shade dried fruit rind (1 Kg) of *Garcinia mangostana* was pulverized to coarse powder, and extracted with methanol (5 L) for 2 hrs at 60-65° C. The solvent was separated from the raw material by filtration. Extraction process was repeated thrice using methanol (2×3 L & 1×2 L). The combined extracts were fine filtered and concentrated under reduced pressure and allowed to precipitate at ambient temperature. The solid separated was filtered to give a dry powder (165 g, α-Mangostin: 32% and γ-Mangostin: 3%).

Example 6

Purification of α-Mangostin and γ-Mangostin:

The methanol extract (90 g) of *G. mangostana* having 32% α-mangostin was subjected to chromatography over a silica column using eluants of increasing polarity from chloroform to methanol. The fractions eluted with 10-15% methanol/chloroform were monitored and the fraction containing α-mangostin were combined and evaporated under vacuum and the residue was crystallized from dichloromethane/methanol mixture to obtain a residue (20 g) containing 99% of α-mangostin. The fractions eluted with 25% methanol/chloroform were monitored and the fraction containing γ-mangostin were combined and evaporated under vacuum and the residue was crystallized from dichloromethane/methanol mixture to residue (2.1 g) containing 99% of γ-mangostin.

Example 7

Process for Preparing Composition 1A, Composition 1B, Composition 1C and Composition 1D Composition-1A was prepared by mixing unit doses of the following components: Three parts of *Sphaeranthus indicus* ethyl acetate extract (LI/DD-II/054A/01, 3 g) and one part of *Garcinia mangostana* methanol extract (AR933, 1 g).

Composition 1B was prepared by mixing unit doses of the following components: One part of *Sphaeranthus indicus* ethyl acetate extract (1 g) and three parts of *Garcinia mangostana* methanol extract (3 g).

Composition 1C was prepared by mixing unit doses of the following components: one part of *Sphaeranthus indicus* methanol extract (1 g) and three parts of *Garcinia mangostana* methanol extract (3 g).

Composition 1D was prepared by mixing unit doses of the following components: three parts of *Sphaeranthus indicus* methanol extract (3 g) and one part of *Garcinia mangostana* methanol extract (1 g)

Example 8

Process for Preparing Compositions 2A, 2B and 2C

Composition 2A: Composition 2A was prepared by mixing unit doses of the following components:
Two parts of *Sphaeranthus indicus* ethyl acetate extract (2 g) and
One part of *Garcinia mangostana* methanol extract (1 g)
Composition 2B: Composition 2B was prepared by mixing unit doses of the following components:
One part of *Sphaeranthus indicus* ethyl acetate extract (1 g) and
Two parts of *Garcinia mangostana* methanol extract (2 g)
Composition 2C: Composition 2C was prepared by mixing unit doses of the following components:
One part of *Sphaeranthus indicus* ethyl acetate extract (1 g) and
One part of *Garcinia mangostana* methanol extract (1 g)

Example 9

Process for Preparing Compositions 2D and 2E

Composition 2D: Composition 2D was prepared by mixing unit doses of the following components:
Four parts of *Sphaeranthus indicus* ethyl acetate extract (4 g) and
One part of *Garcinia mangostana* methanol extract (1 g).
Composition 2E: Composition 2E was prepared by mixing unit doses of the following components:
One part of *Sphaeranthus indicus* ethyl acetate extract (1 g) and
Four parts of *Garcinia mangostana* methanol extract (4 g).

Example 10

Inhibition of Matrix Metalloproteinase-1 (MMP-1) Production by Gorakhmundi Extract MMP-1 was evaluated in PMA induced human melanoma cells, A2058. Briefly, the cells were cultured in Dulbecco's Modified Eagles Medium (DMEM) with 2 mM Glutamine, 100 U/mL penicillin, 100 mg/mL streptomycin and 10% fetal bovine serum (Hyclone, Logan, Utah). Five thousand cells per well were seeded into a 96-well cell culture plate (Corning, USA) one day before the experiment. The culture media was replaced with fresh DMEM containing 10% fetal bovine serum. *Sphaeranthus indicus* ethyl acetate extract (LI/DD-II/054A/01) was serially diluted in medium, ranging from 0.1 to 10 µg/ml and was pre-incubated with cells for 2 hour at 5% CO2 at 37° C., and then stimulated with 50 mM of PMA for 24 hours. The supernatant was harvested and used to measure MMP-1 production by MMP-1 ELISA Development Kit (R&D System, Minneapolis, Minn., USA). The MMP-1 concentration in culture supernatant was estimated quantitatively by interpolating the optical densities into the standard curve generated from known concentrations of MMP-1.

Figure 2:
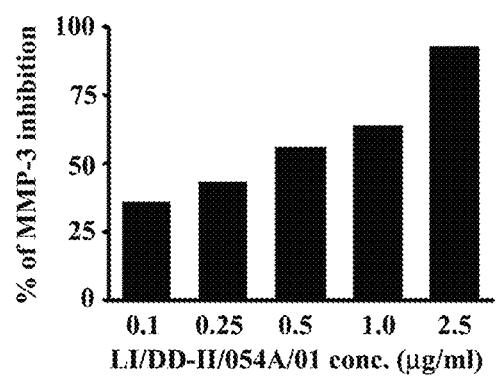
FIG. 2: Illustrates Bar diagram which shows percent reduction in MMP-3 concentration in A549 human lung tumor cell culture supernatants obtained by *Sphaeranthus indicus* ethyl acetate extract (LI/DD-II/054A/01). A549 cells were induced with 10 ng/ml human IL-1β in absence or presence of different concentrations of LI/DD-II/054A/01 for 24 h as indicated. Secreted MMP-3 concentration in the cell free culture supernatants was measured using MMP-3 ELISA Development Kit (R&D System, Minneapolis, Minn., USA). The MMP-3 concentration in culture supernatants was estimated quantitatively from the standard curve generated using known concentrations of MMP-3. Percentage of MMP-3 inhibition at each concentration of test compound was calculated from the formula: {(Conc. of MMP-3 in IL-1β induced−Conc. of MMP-3 in the test well)×100}÷Conc. of MMP-3 in IL-1β induced wells.

The inhibitory effect at different concentration of ethyl acetate extract (LI/DD-II/054A/01) of *Sphaeranthus indicus* is depicted in FIG. 1. The inhibitory concentration for 50% inhibition ($IC_{50}$) of MMP-1 was calculated from the plot constructed by plotting percentage inhibition against concentration. The ethyl acetate extract (LI/DD-II/054A/01) of *Sphaeranthus indicus* showed an $IC_{50}$ value of 10.14 µg/mL. Using a similar procedure the $IC_{50}$ value of the pure compound 7-hydroxyfrullanolide (LI054A01) was found to be 1.2 µg/mL.

Example 11

Inhibition of Matrix Metalloproteinase-3 (MMP-3) Production by Gorakhmundi Extract MMP-3 was evaluated in Interleukin-1β induced human lung tumor cell line A549. Briefly, the cells were cultured in DMEM with 2 mM Glutamine, 100 U/mL penicillin, 100 mg/mL streptomycin and 10% fetal bovine serum (Hyclone, Logan, Utah). Five thousand cells per well were seeded into a 96-well cell culture plate (Corning, USA) one day before the experiment. The culture media was replaced with fresh DMEM containing 10% fetal bovine serum. *Sphaeranthus indicus* ethyl acetate extract (LI/DD-II/054A/01) was serially diluted in medium, ranging from 0.1 to 10 µg/ml and was pre-incubated with cells for 2 hour at 5% $CO_2$, at 37° C., and then stimulated with 10 ng/mL human IL-1β (R&D System, Minneapolis, Minn.) for 24 hours. The supernatant was harvested and used to measure MMP-3 production by ELISA development kit (R&D System, Minneapolis, Minn., USA). The MMP-3 concentration in culture supernatant was estimated quantitatively by interpolating the optical densities into the standard curve generated from known concentrations of MMP-3. The inhibitory concentration for 50% inhibition ($IC_{50}$) of MMP-3 was calculated from the plot constructed by plotting percentage inhibition against concentration. The ethyl acetate extract (LI/DD-II/054A/01) of *Sphaeranthus indicus* showed an $IC_{50}$ value of 0.36 µg/mL against MMP-3. The data is summarized in FIG. 2. Using a similar procedure the $IC_{50}$ value of the pure compound 7-hydroxyfrullanolide (LI054A01) was found to be 0.075 µg/mL.

Example 12

Assessment of Inhibition of Lipid Accumulation in Differentiated Adipocytes by *Sphaeranthus indicus* Ethyl Acetate Extract (LI/DD-II/054A/01) and 7-Hydroxyfrullanolide (LI054A01)

One hundred thousand 3T3-L1 Human pre-adipocyte cells in Dulbecco's Modified Eagles Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium containing 10 µg/ml insulin, 1.0 µM dexamethasone, and 0.5 mM isobutylmethylxanthine (IBMX) for 48 h. After this the medium was replaced by DMEM containing 10 µg/ml insulin and incubated for 3 days. Then the differentiating cells were treated 10 µg/ml of *Sphaeranthus indicus* ethyl acetate extract (LI/DD-II/054A/01) and 0.5 µg/ml of 7-hydroxyfrullanolide (LI054A01) and maintained in the medium for another 3-5 days. The cells incubated with 0.1% DMSO were considered as the vehicle control. After the incubation period, cells were washed with phosphate buffered saline (PBS) and fixed with 10% buffered formalin for 1 h at room temperature. One small aliquot of cell suspension was separated for cell counting in hemocytometer chamber. Fixed cells were stained with Oil Red O solution to measure the cellular neutral lipid accumulation. Briefly, cells were washed with PBS, fixed with 10% buffered formalin and stained with Oil Red O solution (0.5 g in 100 ml isopropanol) for 10 min. After removing the staining solution, the dye retained in the cells will be eluted into isopropanol and OD measured at 550 nm. The inhibition of fat accumulation in the treated cells was compared with the mock treated differentiated adipocytes. The treated and control cells were also analyzed and compared for inhibition of lipid accumulation visually under microscope and recorded digitally in suitable image capture system. The anti-adipogenic activities shown by *Sphaeranthus Indicus* ethyl acetate extract (LI/DD-II/054A/01) and LI054A01 are summarized in the following table.

Anti-Adipogenic Activity of *Sphaeranthus indicus*

TABLE I

| S. No | Name of the product | % inhibition of lipid accumulation |
|---|---|---|
| 1 | LI/DD-II/054A/01 | 65.9% at 10 µg/ml |
| 2 | LI054A01 | 68.7% at 0.5 µg/ml |

Example 13

Assessment of Pro-Lipolytic Activity of *Sphaeranthus Indicus* Ethyl Acetate Extract (LI/DD-II/054A/01) and 7-Hydroxyfrullanolide (LI054A01) in Differentiated Adipocytes The lipolytic activity was assessed in mature adipocytes as per the procedure of Chemicon International, USA, by measuring free glycerol secreted into the culture medium. One hundred thousand 3T3-L1 Human pre-adipocyte cells in Dulbecco's Modified Eagles Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium containing 10 µg/ml insulin, 1.0 µM dexamethasone, and 0.5 mM isobutylmethylxanthine (IBMX). The cells were differentiated for 5 days and then the culture medium was removed. The monolayer was washed twice with wash solution (Hank's balanced salt solution), and then 250 µL of incubation solution (Hank's balanced salt solution plus 2% bovine serum albumin) was added to the wells in triplicate in presence or absence of *Sphaeranthus indicus* ethyl acetate extract (LI/DD-II/054A/01) and 7-hydroxyfrullanolide (LI054A01), and the cells were further incubated for 16 h. To measure lipolysis, 200 µL of free glycerol assay reagent was added to 25 µL of culture supernatants and controls containing glycerol standard. The samples and the controls were incubated for 15 min, and the absorbance was read at 540 nm. A standard curve constructed from the glycerol was used to calculate the concentration of free glycerol in the culture supernatants. The percentage increase in glycerol concentration in the sample solutions compared to the control containing the known concentrations of glycerol corresponds to the percentage acceleration of lipolysis by LI/DD-II/054A/01 or LI054A01. The percentage increase in lipolysis accelerated by LI/DD-II/054A/01 and LI054A01 are summarized table II.

Pro-Lipolytic Activity of *Sphaeranthus indicus*

TABLE II

| S. No | Name of the product | % acceleration of lipolysis |
|---|---|---|
| 1 | LI/DD-II/054A/01 | 26.7% at 25 µg/ml |
| 2 | LI054A01 | 47.8% at 5 µg/ml |

Example 14

Inhibition of Peroxisome Proliferator-Activated Receptor Gamma (PPARγ) Adipose Differentiation Related Protein (ADRP), CD36, Adipocyte Fatty Acid Binding Protein (aP2), Beta-3 Adrenergic Receptor (β3AR) and Perilipin in 3T3-L1 Adipocytes by *Sphaeranthus indicus* Ethyl Acetate Extract (LI/DD-II/054A/01) and 7-Hydroxyfrullanolide (LI054A01)

Experimental protocol: Mouse pre-adipocyte 3T3-L1 cells are maintained in Dulbecco's Modified Eagles Medium (DMEM) supplemented with 2 mM glutamine, 4.5 g/L glucose and 10% fetal bovine serum. Equal number of cells was plated in each well of 24-well culture plates. Cells were pre-treated separately with 2.5, 5 and 10 µg/mL of LI/DD-II/054A/01 or 1 µg/mL 7-hydroxyfrullanolide for 2 h and followed by addition of differentiation medium containing 500 nM insulin, 1.0 µM dexamethasone, and 0.5 mM isobutylmethylxanthine (IBMX) for 48 h. Thereafter, cells were further incubated with post differentiation medium (DMEM containing 100 nM insulin) in presence or absence of *Sphaeranthus indicus* extract LI/DD-II/054A/01 extract and 7-hydroxyfrullanolide (LI054A01). Finally, the cells were harvested, washed with chilled phosphate buffered saline and lysed with the lysis buffer. The protein extracts were clarified at 14,000 g for 20 min. Protein content was measured in Bradford method by using Coomassie blue dye and cell lysates were stored in aliquots at −80° C. until further use. The modulation of adipocyte differentiation markers such as Peroxisome proliferator-activated receptor gamma (PPARγ), CD36, adipocyte fatty acid binding protein (aP2); and intracellular lipid droplet surface associated protein, perilipin expression were evaluated by immunoblot assay.

Inhibition of protein expression of biomarker molecules adipocytes in presence or absence of *Sphaeranthus indicus* extract LI/DD-II/054A/01 and 7-hydroxyfrullanolide (LI054A01) was evaluated in immunoblot assay. Briefly, equal amount of cell lysates proteins were resolved in 7.5% SDS-PAGE; thereafter, the proteins were transferred to nitrocellulose membrane. After blocking the non-specific sites, the membrane was incubated with either anti-PPARγ, or anti-CD36, or anti-aP2, or anti-β3AR, or anti-ADRP, or anti-perilipin antibody. Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The data is summarized in FIG. 3

Example 15

Inhibition of CD36 Production by *Sphaeranthus indicus* Extract Ethyl Acetate Extract (LI/DD-II/054A/01) and 7-Hydroxyfrullanolide (LI054A01) in Macrophage Cells Experimental protocol: This was evaluated in glucose induced J774, mouse macrophage cells. Briefly, the cells were cultured in DMEM with 2 mM Glutamine, 100 U/mL penicillin, 100 mg/mL streptomycin and 10% fetal bovine serum (Hyclone, Logan, Utah). Equal number of cells was seeded into 35 mm petri dishes (Corning, USA) one day before the experiment. The culture media was replaced with fresh, glucose free DMEM supplemented with 10% fetal bovine serum. *Sphaeranthus indicus* ethyl acetate extract (LI/DD-II/054A/01) was serially diluted in above culture medium, ranging from 1 to 10 µg/ml and LI054A01 was diluted at 1 µg and all cultures were pre-incubated for 2 hours at 5% $CO_2$ at 37° C., and then incubated with 600 mg/dL of glucose for 5 days. The control culture was supplemented with 100 mg/dL glucose. The cells were harvested and lysed with lysis buffer. Cell lysates were clarified at 14,000 g. Protein concentration was measured by Bradford method.

Figure 4:
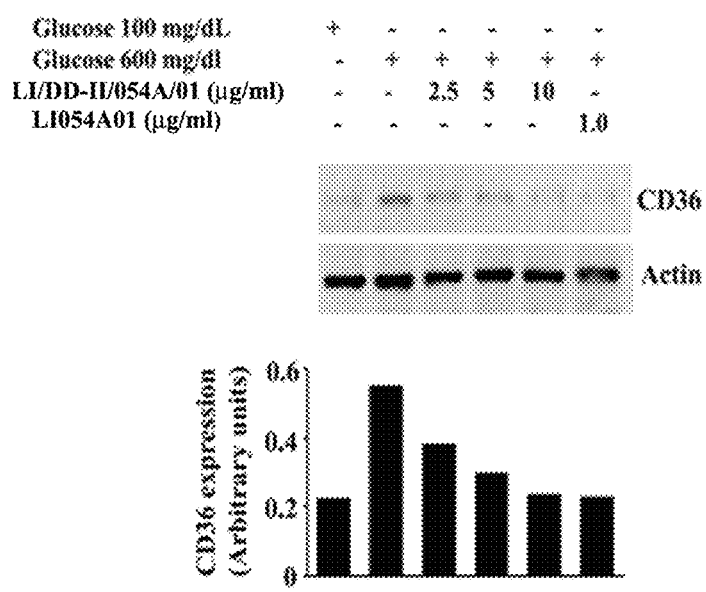
FIG. 4: Illustrates down-regulation of high glucose induced CD36 expression in macrophage cells by *Sphaeranthus indicus* ethyl acetate extract (LI/DD-II/054A/01) and 7-hydroxyfrullanolide (LI054A01). The J774 mouse macrophage cells were exposed to high glucose (600 mg/dL) for 5 days in presence or absence of LI/DD-II/054A/01 at various concentrations or 1 μg/ml of LI054A01 as indicated. The control cultures received low glucose (100 mg/dL). Representative immuno blot assay demonstrates down regulation of CD36 protein. The expression of actin protein is considered as the internal control. Bar diagram shows the CD36 expression normalized with actin protein (lower panel).

Inhibition of CD36 protein expression in high glucose induced J774 macrophage cells in presence or absence of LI/DD-II/054A/01 and LI054A01 was evaluated in immunoblot assay. Briefly, equal amount of cell lysates proteins were resolved in 7.5% SDS-PAGE; thereafter, the proteins were transferred to nitrocellulose membrane. After blocking the non-specific sites, the membrane was incubated with CD36 antibody (R&D Systems, Minneapolis, Minn.). Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The results are summarized in FIG. 4.

Example 16

Assessment of Inhibition of Lipid Accumulation in Differentiated Adipocytes by *Garcinia mangostana* Methanol Extract (AR 933), α-Mangostin and γ-Mangostin The anti-adipogenic activity of *Garcinia mangostana* extract (AR 933), α-mangostin and γ-mangostin were assessed by method as described in example 12 above. The anti-adipogenic activities shown by the extract AR 933, α-mangostin and γ-mangostin are summarized in the following table.

Anti-Adipogenic Activity of *Garcinia mangostana*

TABLE III

| S. No | Name of the product | % inhibition of Lipid accumulation 10 µg/ml |
|---|---|---|
| 1 | α-mangostin | 16.06 |
| 2 | γ-mangostin | 61.57 |
| 3 | G. mangostana (AR 933) | 48.5 |

Example 17

**Assessment of Pro-Lipolytic α-Mangostin, γ-Mangostin and *Garcinia mangostana* Methanol Extract (AR 933) in Differentiated Adipocytes**

The lipolytic activity was assessed in mature adipocytes as described in the Example 13 above. The percentage increase in glycerol concentration in the sample solutions compared to the control containing the known concentrations of glycerol corresponds to the percentage acceleration of lipolysis for the test compounds. The percentage increase in lipolysis accelerated by α-mangostin, γ-mangostin and *Garcinia mangostana* methanol extract (AR 933) are summarized in the following table.

Pro-Lipolytic Activity of *Garcinia mangostana*

TABLE IV

| S. No | Name of the product | % acceleration of lipolysis 25 µg/ml |
|---|---|---|
| 1 | α-mangostin | 156.56 |
| 2 | γ-mangostin | 4.52 |
| 3 | *G. mangostana* (AR 933) | 55.8 |

Example 18

**Inhibition of Alpha-Amylase by *Garcinia* Mangostin Methanol Extract (AR 933), α- and γ-Mangostins**

α-Amylase inhibitory activity was measured using the dinitrosalicylic acid (DNS) method developed by Bernfeld (Methods in Enzymology, 1955, Vol. 1, pp 149-158), improved by Jamieson et al (Journal of Dental Research 1969; 48(3): 483) and adopted for testing inhibitory potential of test substances by M. C. M da Silva et al (2004, Pesq. Agropec. bras., Brasilia, 2004; 39(3); pp 201-208) using 1% soluble starch as substrate.

The test substances (α-mangostin, γ-mangostin and AR 933) were pre-incubated with α-amylase 100 µL (10-25 U/mL) at room temperature for 20 minutes prior to the addition of 100 µL of the substrate solution followed by incubation at 37° C. for 10 minutes. The reactions were stopped by the addition of 200 µL of DNS reagent, followed by color development by placing the tubes in boiling water for 5 minutes. After addition of 3.6 mL distilled water, the absorbance was read at 470 nm. Known α-amylase inhibitor was used as positive control and vehicle was used as negative control. Assays were carried out at least in duplicate. Percentage inhibition will be calculated by comparing mean test OD with mean control OD. {% inhibition= [(COD−TOD)/COD]×100}. The $IC_{50}$ values were calculated by linear regression analysis of the dose response curve. The results are summarized in the following table.

TABLE V

| Compound | $IC_{50}$ (µg/ml) for α-amylase |
|---|---|
| γ-mangostin | 3.88 |
| α-mangostin | 3.99 |
| AR 933 | 5.32 |
| Acarbose | 12.7 |

Example 19

**Inhibition of α-Glucosidase by *Garcinia* Mangostin Methanol Extract (AR 933), α and γ Mangostins**

α-Glucosidase inhibitory activity was measured using the in vitro method developed by D. Prasanth et al., (Fitoterapia 2001, 72, 686-688). In a micro plate well was taken 50 µL of α-glucosidase enzyme (0.4 U/mL), and treated with 90 µL of 100 mM phosphate buffer (pH 7) and 10 µL test substances (α-mangostin, γ-mangostin and AR 933) or vehicle control. The contents were mixed well and the reaction mixtures were incubated at room temperature for 5 min, and then added 50 µL of p-nitrophenyl α-D-glucopyranose (20 mM) as substrate. The contents were mixed well and again incubated at room temperature for 15 min. The reaction was stopped by the addition of 30 µL of sodium carbonate solution (135 mM). The absorbance was measured at 405 nm using micro plate reader. Control and test blank ODs were obtained by replacing enzyme with buffer. Percentage inhibitions were calculated by comparing mean test OD with mean control OD. {% inhibition=[(COD−TOD)/COD]× 100}. The $IC_{50}$ values were calculated by linear regression analysis of the dose response curve.

TABLE VI

| Compound | $IC_{50}$ (µg/ml) for α-glucosidase |
|---|---|
| γ-mangostin | 0.16 |
| α-mangostin | 0.30 |
| AR 933 | 0.29 |
| Green Tea | 1.10 |

Example 20

**Inhibition of PPARγ, ADRP, CD36, aP2, β3AR and Perilipin in 3T3-L1 Adipocytes by *Garcinia mangostana* Extract (AR 933)**

Experimental protocol: Mouse pre-adipocyte 3T3-L1 cells are maintained in Dulbecco's Modified Eagles Medium (DMEM) supplemented with 2 mM glutamine, 4.5 g/L glucose and 10% fetal bovine serum. Equal number of cells was plated in each well of 24-well culture plates. Cells were pre-treated separately with 2.5 and 5 µg/mL of *Garcinia mangostana* methanol extract (AR 933) for 2 h and followed by addition of differentiation medium containing 500 nM insulin, 1.0 µM dexamethasone, and 0.5 mM isobutylmethylxanthine (IBMX) for 48 h. Thereafter, cells were further incubated with post differentiation medium (DMEM containing 100 nM insulin) in presence or absence of *Garcinia mangostana* methanol extract (AR 933). Finally, the cells were harvested, washed with chilled phosphate buffered saline and lysed with the lysis buffer. The protein extracts were clarified at 14,000 g for 20 min. Protein content was measured in Bradford method by using Coomassie blue dye and cell lysates were stored in aliquots at −80° C. until further use. The modulation of adipocyte differentiation markers such as PPARγ, CD36, aP2 and intracellular lipid droplet surface associated protein, perilipin expression were evaluated by immunoblot assay.

Inhibition of protein expression of biomarker molecules adipocytes in presence or absence of *Garcinia mangostana* extract was evaluated in immunoblot assay. Briefly, equal amount of cell lysates proteins were resolved in 7.5% SDS-PAGE; thereafter, the proteins were transferred to nitrocellulose membrane. After blocking the non-specific sites, the membrane was incubated with either anti-PPARγ, or anti-CD36, or anti-aP2, or anti-β3AR, or anti-ADRP, or anti-perilipin antibody. Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The data is summarized in FIG. 5.

Example 21

Assessment of Inhibition of Lipid Accumulation in Differentiated Adipocytes by Compositions 1B, 2C and 2E Comprising LI/DD-II/054A/01 and AR 933

The anti-adipogenic activities of Compositions 1B, 2C and 2E were also assessed by methods as described in example 12 above. The anti-adipogenic activities shown by Compositions 1B, 2C and 2E are summarized in Table VII.

Anti-Adipogenic Activity of Compositions 1B, 2C & 2E

TABLE VII

| S. No | Name of the product | % Inhibition of Lipid accumulation 10 µg/mL |
|---|---|---|
| 1 | Composition 1B (1:3) | 23.6 |
| 2 | Composition 2C (1:1) | 21.5 |
| 3 | Composition 2E (1:4) | 38.6 |

Example 22

Assessment of Pro-Lipolytic Compositions 1B, 2C and 2E Comprising LI/DD-11/054A/01 and AR 933 in Differentiated Adipocytes The lipolytic activity of Compositions 1B, 2C & 2E were assessed in mature adipocytes as described in example 13 above. The percentage increase in glycerol concentration in the sample solutions compared to the control containing the known concentrations of glycerol corresponds to the percentage acceleration of lipolysis by Compositions 1B, 2C & 2E. The percentage increase in lipolysis accelerated by Compositions 1B, 2C and 2E are summarized in the following table Pro-Lipolytic Activity of Compositions 1B, 2C and 2E

TABLE VIII

| S. No | Name of the product | % acceleration of lipolysis 25 µg/ml | % acceleration of lipolysis 50 µg/ml |
|---|---|---|---|
| 1 | Composition 1B (1:3) | 31.7 | 59.8 |
| 2 | Composition 2C (1:1) | 21.9 | 46.9 |
| 3 | Composition 2E (1:4) | 37.95 | 71.4 |

Example 23

Inhibition of PPARγ, ADRP, CD36, aP2, β3AR and Perilipin in 3T3-L1 Adipocytes by Composition 1B Experimental protocol: Mouse pre-adipocyte 3T3-L1 cells are maintained in Dulbecco's Modified Eagles Medium (DMEM) supplemented with 2 mM glutamine, 4.5 g/L glucose and 10% fetal bovine serum. Equal number of cells was plated in each well of 24-well culture plates. Cells were pre-treated with 5 µg/ml of either LI/DD-II/054A/01 or AR 933 or composition 1B for 2 h and followed by addition of differentiation medium containing 500 nM insulin, 1.0 µM dexamethasone, and 0.5 mM isobutylmethylxanthine (IBMX) for 48 h. Thereafter, cells were further incubated with post differentiation medium (DMEM containing 100 nM insulin) in presence or absence of composition 1B. Finally, the cells were harvested, washed with chilled phosphate buffered saline and lysed with the lysis buffer. The protein extracts were clarified at 14,000 g for 20 min. Protein content was measured in Bradford method by using Coomassie blue dye and cell lysates were stored in aliquots at −80° C. until further use. The modulation of adipocyte differentiation markers such as Peroxisome proliferator activator receptor-gamma (PPAR-γ), CD36, adipocyte fatty acid binding protein (aP2); and intracellular lipid droplet surface associated protein, perilipin expression were evaluated by immunoblot assay.

Inhibition of protein expression of biomarker molecules adipocytes in presence or absence of composition 1B was evaluated in immunoblot assay. Briefly, equal amount of cell lysates proteins were resolved in 7.5% SDS-PAGE; thereafter, the proteins were transferred to nitrocellulose membrane. After blocking the non-specific sites, the membrane was incubated with either anti-PPARγ, or anti-CD36, or anti-aP2, or anti-β3AR, or anti-ADRP, or anti-perilipin antibody. Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The data is summarized in FIG. 6.

Example 24

Down-Regulation of Production of Atherosclerotic Marker Proteins by Composition 1B Experimental protocol: Production inhibition of atherosclerotic marker proteins such as CD36, monocytes chemoattractant protein-1 (MCP-1), and oxidized Low density lipoprotein (Ox-LDL) by composition-1B was evaluated in high glucose induced J774, mouse macrophage cells. Briefly, the cells were cultured in DMEM with 2 mM Glutamine, 100 U/mL penicillin, 100 mg/mL streptomycin and 10% fetal bovine serum (Hyclone, Logan, Utah). Equal number of cells was seeded into 35 mm petri dishes (Corning, USA) one day before the experiment. The culture media was replaced with fresh, glucose free DMEM supplemented with 10% fetal bovine serum. Cells were pre-incubated with 5 ug/ml of either LI/DD-II/054A/01 or AR 933 or composition 1B for 2 h at 37° C. with 5% CO2, and then incubated with 600 mg/dL of glucose for 5 days. The control culture was supplemented with 100 mg/dL glucose. The cells were harvested and lysed with lysis buffer. Cell lysates were clarified at 14,000 g. Protein concentration was measured by Bradford method.

Inhibition of marker proteins expression in high glucose induced J774 macrophage cells in presence or absence of composition 1B was evaluated in immunoblot assay. Briefly, equal amount of cell lysates proteins were resolved in 7.5% SDS-PAGE; thereafter, the proteins were transferred to nitrocellulose membrane. After blocking the non-specific sites, the membrane was incubated with either CD36, or MCP-1 or Ox-LDL specific antibody (R&D Systems, Minneapolis, Minn.). Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The results are summarized in FIG. 7.

Example 25

Modulation of Adiponectin by LI/DD-II/054A/01, AR 933 and Composition 1B

Modulation of adiponectin protein by LI/DD-II/054A/01 or AR 933 or composition-1B in 3T3-L1 adipocytes was evaluated in Western immunoblot assay. The cell culture, treatment protocol and immunoblot assay methodology were the same as described in Example 23. FIG. 8 summarizes the enhancement of adiponectin protein expression in 3T3-L1 mature adipocytes by composition 1B or its individual components such as LI/DD-II/054A/01 or AR 933.

Example 26

Down Regulation of Protein Tyrosine Phosphatase-1B (PTP-1B) in 3T3-L1 Preadipocytes by LI/DD-II/054A/01 or AR 933 or Composition 1B:

The 3T3-L1 preadipocytes were cultured in Dulbecco's Modified Eagles Medium (DMEM) supplemented with 2 mM glutamine, 4.5 g/L glucose and 10% fetal bovine serum. Equal number of cells was plated in each 35 cm$^2$ cell culture dish overnight. Plates were washed with serum free and phenol red free DMEM, then the cultures were pre treated with 5 μg/ml of either LI/DD-II/054A/01 or AR 933 or composition 1B in FBS free and phenol red free DMEM containing 0.2% BSA and 1 g/liter glucose. The cell lysates proteins were extracted in cell lysis buffer and protein concentrations were measured by Bradford reagent. The modulation of PTP-1B expression in cell lysates were analyzed by immunoblot assay using anti-PTP-1B antibody following the method as described in example 23. FIG. 9 shows down regulation of PTP 1B protein expression in LI/DD-II/054A/01 or AR 933 or composition 1B treated 3T3-L1 preadipocytes.

Example 27

In Vivo Efficacy of *Sphaeranthus indicus* Ethyl Acetate Extract (LI/DD-II/054A/01) Against Metabolic Disorders Efficacy of the *Sphaeranthus indicus* ethyl acetate extract (LI/DD-II/054A/01) was tested in high fat, high cholesterol, high salt and high sucrose diet induced model of metabolic syndrome.

Induction: A batch of 12 Sprague Dawley Rats was randomly divided into 2 groups, each comprised of 6 animals. Animals were acclimatized for 7 days prior to study initiation. Metabolic syndrome was induced by feeding the rats with the metabolic syndrome diet containing 32 g of roasted bengal gram, 27 g of sucrose, 17 g of milk powder, 5 g of mineral salt mixture, 1 g of yeast, 2 g of butter, 11 g of groundnut oil and 5 g of cholesterol per 100 g of the diet for 8 weeks.

Treatment: Following 8 weeks induction phase, the animals were treated orally (using oral feeding gavage) with allocated test substance or vehicle daily for 8 weeks. The treatment group animals were supplemented orally with 250 mg/kg body weight of LI/DD-II/054A/01 in 10 mL of 0.5% CMC in water for further 8 weeks. The control group of animals received only the vehicle (10 mL of 0.5% CMC in water) during this period. During the treatment phase, all animals were provided with the standard rodent diet till the end of the study.

Body weights: Body weight of individual animal was recorded weekly for the entire duration of the study. Mean body weights for the treatment group and control group were determined. The body weight gain was calculated at the end of 1$^{st}$ week, 4$^{th}$ week and 8$^{th}$ week after initiation of treatment in comparison to initial body weight. In comparison to the control group, LI/DD-II/054A/01 at 250 mg/kg dose exhibited highly potent and statistically significant ($p<0.01$) reduction in body weight gain (66.04%) in comparison to control group. The results of body weight gain for the treatment groups and control group are summarized in FIGS. 10A and 10B.

Fat Tissue Weight:

Abdominal and epididymal fat were isolated and weighed at the termination of the study and the results were represented in Table-9. Abdominal and epididymal fat weights in the treatment group are lower, when compared to those in the control group. The total fat was significantly reduced ($p<0.05$) in the treatment group supplemented with LI/DD-II/054A/01.

Weight of Fat Tissues Isolated from Abdomen and Epididymal Area of Rats.

TABLE 9

| Treatment | Abdominal fat (g) | Epididymal fat (g) | Total fat (g) |
|---|---|---|---|
| Control (10 mL/kg) | 4.52 ± 1.16 | 4.18 ± 1.56 | 8.70 ± 2.52 |
| LI/DD-II/054A/01 (250 mg/kg) | 2.28 ± 0.78 | 3.07 ± 0.74 | 5.36 ± 0.89 |

Values Expressed as Mean Weight±SD

Serum Biochemistry: Blood sampling was done via sinus orbital plexus under mild anesthesia, before induction, before initiation of treatment and after completion of treatment. Various biochemical parameters including lipid profile were evaluated using biochemistry reagents supplied by Human, Germany, in an automated clinical chemistry analyzer HumaStar300, Make: Human, Germany. Mean values of the biochemical parameters especially serum cholesterol levels and triglycerides levels were estimated before induction, after induction/before treatment and after treatment. Supplementation of LI/DD-II/054A/01 at 250 mg/kg resulted in improvement in fat profile with 15.3, 12.7 and 22.9 percentage reductions respectively in serum cholesterol, LDL and triglycerides.

Estimation of Biomarker Adiponectin: The serum adiponectin concentration for the control and treatment groups of animals were assessed using double antibody based sandwich rat adiponectin ELISA kit. The assay was performed following the instructions provided by the manufacturer (Linco Research, USA). The sensitivity of the assay is 0.155 ng/ml. Adiponectin assay revealed that supplementation of LI/DD-II/054A/01 at a dose of 250 mg/day/kg body weight for 8-weeks resulted in significant (p=0.00618) improvement in serum adiponectin concentration, in comparison with the baseline. The control group, however, did not show improvement in serum adiponectin concentration. The results are summarized in FIG. 11.

The Homeostasis Model Assessment (HOMA): The HOMA index was calculated based on serum insulin and glucose levels, using the following formula: Fasting insulin concentration ($\mu$U/mL)×Fasting glucose concentration (mmol/L)/22.5.

The supplementation of treatment group of rats with a daily dose of 250 mg/kg body weight for 8-week treatment period resulted in significant reduction of HOMA index compared to control group. The data is presented in FIG. 12.

Example 28

Synergistic Anti-Obesity Activity of Composition 1D Comprising *Sphaeranthus indicus* Methanol Extract (LI/DD-II/054A/03) and *Garcinia mangostana* Methanol Extract (AR 933) in 3:1 Ratio Efficacy of LI/DD-II/054A/03, AR 933 and composition 1D were tested against High Fat Diet induced obesity model of Sprague-Dawley rats. Induction: Selected healthy Sprague-Dawley rats were randomly assigned to control or various treatment groups (n=7). All the animals allocated in the obesity study were made experimentally obese through dietary intervention during the entire eight weeks induction period by feeding high fat diet ad libitum containing Bengal gram 32 g, Wheat floor 15 g, Yeast 1 g, Butter 2 g, Ground nut oil 8 g, Casein 5 g, Vanaspathi 20 g, Vitamin mix 05 g, Milk powder 12 g and Mineral Salt mixture 4.5 g per 100 g of high fat diet.

Treatment: Following 8 weeks of induction phase, the animals were treated orally (using oral feeding gavage) with allocated test substances or vehicle daily for 8 weeks. The animals of treatment groups were supplemented with 100 mg or 250 mg/kg body weight of LI/DD-II/054A/03 or 250 mg/kg body weight of AR 933 or 250 mg/kg body weight of composition 1D in 10 mL of 0.5% CMC in water for further 8 weeks. The control group of animals received only the vehicle (10 mL of 0.5% CMC in water) during this period. During the treatment phase, all animals were provided with the standard rodent diet till the end of the study.

Body weights: Body weight of individual animal was recorded weekly during the entire duration of the study. Mean body weights for the treatment group and control group were determined. The body weight gain was calculated at the end of $1^{st}$ week, $4^{th}$ week and $8^{th}$ week after initiation of treatment in comparison to initial body weights. LI/DD-II/054A/03 dose dependently inhibited the body weight gain in high fat diet induced obese rats. It exhibited 46.3% reduction in body weight gain in the treatment group supplemented with 100 mg/kg body weight of LI/DD-II/054A/03. AR 933 and LI/DD-II/054A/03 at a dose of 250 mg/kg exhibited 40% and 80.1% reductions in body weight gain respectively. However, the composition 1D at the same dose level i.e. at 250 mg/kg exhibited significantly better reduction in body weight gain (89%) compared to its individual ingredients. The results of body weight gain for the treatment groups and control group are summarized in FIG. 13

Food and water consumption were recorded daily and fasting blood samples were collected before initiation, after $4^{th}$ week and $8^{th}$ week (termination) of the study.

Those of ordinary skill in the art will appreciate that changes could be made to the embodiments described above without departing from the broad inventive concept thereof. It is understood, therefore, that this invention is not limited to the particular embodiments or examples disclosed, but is intended to cover modifications within the objectives and scope of the present invention as defined in the specification.

What is claimed is:

1. A method of controlling or treating a metabolic disorder, comprising administering an effective amount of a biologically active composition to a patient in need thereof, said biologically active composition comprising effective amounts of:
   a first component consisting of:
      a.) from 20 to 80 wt. % of an extract of *Sphaeranthus indicus* flower heads, wherein said extract is at least one of:
         a solvent extract obtained by extraction with a solvent selected from the group consisting of: hexane, dichloromethane, chloroform, ethyl acetate, acetone, methanol, ethanol, n-butanol, isopropanol, methyl isobutyl ketone, and mixtures thereof; and
         an organic solvent or aqueous solvent extract of *Sphaeranthus indicus* flower heads, wherein said organic solvent or aqueous organic solvent extract contains from 8% to 21% 7-hydroxyfrullanolide; and
      b.) from 20 to 80 wt. % of an organic solvent or aqueous organic solvent extract of *Garcinia mangostana* fruit rind; and optionally
   at least one second component selected from the group consisting of i) biologically active components from plants, animals and microorganisms; ii) pharmaceutically acceptable active ingredients; iii) vitamins; iv) minerals, v) vehicles; vi) carriers; vii) diluents, and viii) mixtures thereof,
   wherein the metabolic disorder is selected from the group consisting of diabetes, hypercholesteremia, hyperlipidemia, and a combination thereof.

2. The method of claim 1, wherein the first component consists of:
   from 20 to 80 wt. % of said solvent extract of *Sphaeranthus indicus* flower heads, wherein said solvent extract is obtained by extraction with a solvent selected from the group consisting of hexane, dichloromethane, chloroform, ethyl acetate, acetone, methanol, ethanol, n-butanol, isopropanol, methyl isobutyl ketone, and mixtures thereof; and from 20 to 80 wt. % of an organic solvent or aqueous organic solvent extract of *Garcinia mangostana* fruit rind.

3. The method of claim 1, wherein said solvent extract of *Sphaeranthus indicus* flower heads comprises at least one frullanolide or eudesmanoid sesquiterpene compound selected from the group consisting of 7-hydroxyfrullanolide; 11α,13-dihydro-3α,7α-dihydroxy-4,5-epoxy-6β,7-eudesmanolide; 11α,13-dihydro-7α-acetoxy-3β-hydroxy-6β,7-eudesm-4-enolide; 3-keto-β-eudesmol; 11α,13-dihydro-3α,7α-dihydroxyeudesm-4-en-6α,12-olide; 11α,13-dihydro-3α,7α-dihydroxy frullanolide; 11α,13-dihydro-7α,13-dihydroxy frullanolide; 11α,13-dihydro-7α-hydroxy-13-methoxyfrullanolide; 2α,7α-dihydroxy-4-en-11,13-dihydroeudesm-6,12-olide; 2α-hydroxycostic acid; 3-keto-7α-hydroxyeudesm-4-en-6,12-olide (cryptomeridiol); 4-epicryptomeridiol; sphaeranthanolide; 2α-hydroxysphaerantholide; 2α-acetoxysphaerantholide; 2α,7α-dihydroxysphaerantholide; 2α-acetoxy-7α-hydroxysphaerantholide; and 2α-acetoxy-5α-hydroxyisosphaerantholide and mixtures thereof.

4. The method of claim 1, wherein said extract of *Garcinia mangostana* fruit rind comprises:
α-mangostin in an amount of from 0.01% to 95%;
γ-mangostin in an amount of from 0.01% to 95%; or
a mixture of α-mangostin and γ-mangostin in an amount of from 0.01% to 95%.

5. The method of claim 1, wherein said extract of *Sphaeranthus indicus* flower heads comprises at least one frullanolide or eudesmanoid sesquiterpene compound.

6. The method of claim 1, wherein said extract of *Garcinia mangostana* fruit rind inhibits at least one of:
carbohydrate breakdown enzymes selected from the group consisting of alpha-amylase, alpha-glucosidase, and mixtures thereof; and
adipogenesis.

7. The method of claim 1, wherein the biologically active components from plants, animals and microorganisms have a health benefit selected from the group consisting of anti-diabetic activity, anti-hyperglycemic activity, hypolipidemic activity, anti-obesity activity, anti-hypertensive activity, anti-platelet aggregation activity, anti-infective activity, anti-atherosclerotic activity and antiinflammatory activity, anti-oxidant activity and bio-enhancing activity.

8. The method of claim 1, wherein the first component consists of:
from 20 to 80 wt. % of said organic solvent or aqueous solvent extract of *Sphaeranthus indicus* flower heads, wherein said organic solvent or aqueous organic solvent extract contains from 8% to 21% 7-hydroxyfrullanolide; and
from 20 to 80 wt. % of an organic solvent or aqueous organic solvent extract of *Garcinia mangostana* fruit rind.

9. The method of claim 1, wherein the first component consists of:
from 25 to 75 wt. % of said solvent extract of *Sphaeranthus indicus* flower heads, and
from 75 to 25 wt. % of an organic solvent or aqueous organic solvent extract of *Garcinia mangostana* fruit rind.

10. The method of claim 1, wherein the first component consists of:
from 33 to 67 wt. % of said solvent extract of *Sphaeranthus indicus* flower heads, and
from 67 to 33 wt. % of an organic solvent or aqueous organic solvent extract of *Garcinia mangostana* fruit rind.

* * * * *